United States Patent
Robinson et al.

(10) Patent No.: US 11,224,348 B2
(45) Date of Patent: Jan. 18, 2022

(54) IMPLANTABLE DEVICES AND RELATED METHODS FOR MONITORING PROPERTIES OF CEREBROSPINAL FLUID

(71) Applicant: JSR Research, LLC, Macon, GA (US)

(72) Inventors: Joe Sam Robinson, Cleveland, OH (US); Tigran Khachatryan, Macon, GA (US)

(73) Assignee: JSR Research, LLC, Macon, GA (US)

( * ) Notice: Subject to any disclaimer, the term of this patent is extended or adjusted under 35 U.S.C. 154(b) by 0 days.

(21) Appl. No.: 17/265,759

(22) PCT Filed: Aug. 20, 2019

(86) PCT No.: PCT/US2019/047215
§ 371 (c)(1),
(2) Date: Feb. 3, 2021

(87) PCT Pub. No.: WO2020/041275
PCT Pub. Date: Feb. 27, 2020

(65) Prior Publication Data
US 2021/0161406 A1    Jun. 3, 2021

Related U.S. Application Data

(60) Provisional application No. 62/720,600, filed on Aug. 21, 2018, provisional application No. 62/728,288, filed on Sep. 7, 2018.

(51) Int. Cl.
*A61B 5/0205* (2006.01)
*A61B 5/00* (2006.01)
(Continued)

(52) U.S. Cl.
CPC ........ *A61B 5/02055* (2013.01); *A61B 5/0031* (2013.01); *A61B 5/032* (2013.01);
(Continued)

(58) Field of Classification Search
CPC ... A61B 5/02055; A61B 5/0031; A61B 5/032; A61B 5/1114; A61B 5/1126;
(Continued)

(56) References Cited

U.S. PATENT DOCUMENTS 4,593,703 A * 6/1986 Cosman ............... A61B 5/0002
                                                        600/438
6,533,733 B1   3/2003 Ericson et al.
(Continued)

OTHER PUBLICATIONS

PCT Search Report and Written Opinion for PCT Application No. PCT/US2019/047215 dated Oct. 29, 2019 (32 pages).
(Continued)

*Primary Examiner* — Andrew J Mensh
(74) *Attorney, Agent, or Firm* — Eversheds Sutherland (US) LLP

(57) ABSTRACT

Embodiments of the present disclosure provide an implantable device for monitoring properties of cerebrospinal fluid of a patient. In one embodiment, the device may include a housing, a processor, a support member, one or more sensors, and a data storage. The sensors may be in communication with the processor and configured to detect one or more properties of cerebrospinal fluid. The device may be configured for transmitting the data and receiving instructions by an operator for the delivery of a therapeutic agent or imaging agent from a reservoir disposed within the housing in operable communication with a pump.

26 Claims, 7 Drawing Sheets

(51) Int. Cl.
*A61B 5/11* (2006.01)
*A61B 5/145* (2006.01)
*A61B 5/03* (2006.01)
*A61B 5/1455* (2006.01)
*A61B 5/1473* (2006.01)
*A61B 5/024* (2006.01)

(52) U.S. Cl.
CPC .......... *A61B 5/1114* (2013.01); *A61B 5/1126* (2013.01); *A61B 5/1473* (2013.01); *A61B 5/14546* (2013.01); *A61B 5/14553* (2013.01); *A61B 5/4076* (2013.01); *A61B 5/4839* (2013.01); *A61B 5/686* (2013.01); *A61B 5/024* (2013.01); *A61B 2560/0214* (2013.01); *A61B 2562/0219* (2013.01); *A61B 2562/0247* (2013.01); *A61B 2562/0271* (2013.01); *A61B 2562/06* (2013.01)

(58) Field of Classification Search
CPC .......... A61B 5/14546; A61B 5/14533; A61B 5/1473; A61B 5/4076; A61B 6/4839; A61B 5/686; A61B 5/024; A61B 2560/0214; A61B 2562/0214; A61B 2562/0219; A61B 2562/0247; A61B 2562/0271; A61B 2562/06

USPC ........................................................ 600/301
See application file for complete search history.

(56) References Cited

U.S. PATENT DOCUMENTS

| | | | |
|---|---|---|---|
| 8,506,514 | B2 | 8/2013 | Pedersen et al. |
| 8,894,584 | B2 | 11/2014 | Swoboda et al. |
| 2006/0020239 | A1 | 1/2006 | Geiger et al. |
| 2009/0143673 | A1* | 6/2009 | Drost ................... G01F 1/662 600/437 |
| 2010/0022896 | A1* | 1/2010 | Yadav ................... A61B 5/05 600/488 |
| 2012/0053508 | A1* | 3/2012 | Wu ................... A61N 1/36078 604/20 |
| 2012/0238835 | A1 | 9/2012 | Hyde et al. |

OTHER PUBLICATIONS

Chapter II Demand, Amendment Under PCT Article 34 and Reply to Written Opinion for PCT Application No. PCT/US2019/047215 filed Mar. 18, 2020 (44 pages).

* cited by examiner

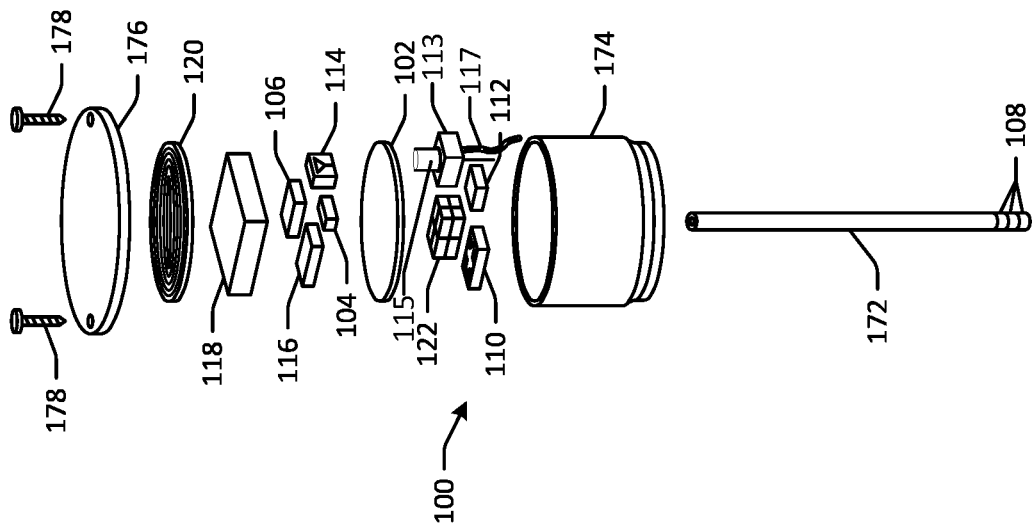
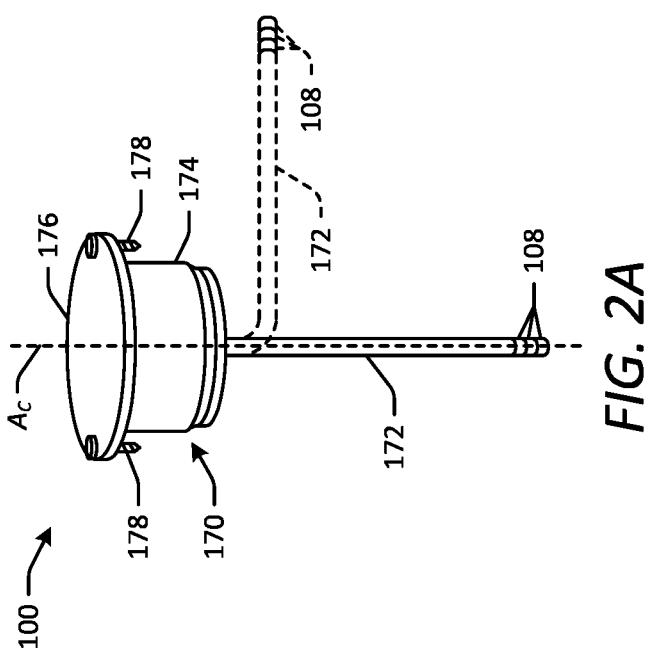
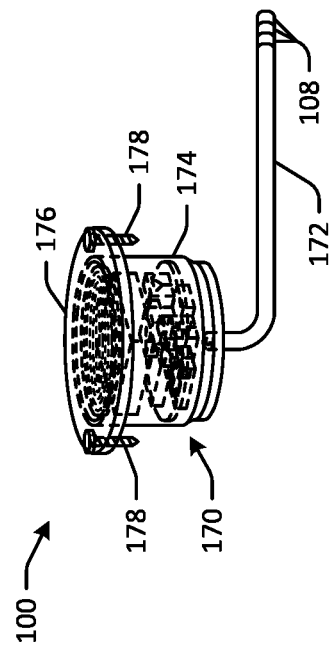
FIG. 2C
FIG. 2A
FIG. 2B

IMPLANTABLE DEVICES AND RELATED METHODS FOR MONITORING PROPERTIES OF CEREBROSPINAL FLUID

CROSS REFERENCE TO RELATED APPLICATIONS

This application claims the priority benefit of PCT/US2019/047215 filed Aug. 20, 2019 which claims priority benefit of U.S. Provisional Application Nos. 62/720,600 and 62/728,288, filed Aug. 21, 2020 and Sep. 7, 2018, respectively. The entire contents of which are incorporated by reference.

FIELD OF THE DISCLOSURE

The present disclosure relates generally to medical devices and methods for evaluating properties of body fluids of a patient and more particularly to implantable devices and related methods of using such devices to monitor properties of cerebrospinal fluid to facilitate diagnosis and/or treatment of various neurological pathologies.

BACKGROUND OF THE DISCLOSURE

Cerebrospinal fluid (CSF), which is present in the brain and the spinal cord of the human body, provides several beneficial functions. For example, CSF provides a buoyancy function in that the human brain is suspended in CSF, which allows the brain to maintain its density without being impaired by its own weight. Without CSF support of the brain, blood supply to the brain would be compromised and neurons within the lower sections of the brain would be damaged. Additionally, CSF present in the brain functions as a fluid buffer in a manner similar to a shock absorber, protecting the brain tissue from certain forms of mechanical injury. CSF present in the brain also provides a vital function in cerebral autoregulation of cerebral blood flow, which inhibits brain ischemia, a condition that occurs when blood flow to the brain is insufficient to meet metabolic demand. For example, in some instances, the amount of CSF present within the skull may be decreased, thereby decreasing total intracranial pressure (ICP) and facilitating blood perfusion. CSF further provides a homeostasis function, as CSF allows for regulation of the distribution of substances between cells of the brain, and neuroendocrine factors, to which slight changes can cause problems with or damage to the nervous system. Finally, CSF facilitates the removal of waste products from the brain and is critical in the lymphatic system of the brain. In particular, metabolic waste products diffuse into CSF and then are removed into the bloodstream as CSF is absorbed.

Current understanding of CSF circulation within the human body is limited and a subject of debate among researchers. Recent evidence indicates that CSF circulation is quite variable and depends upon a number of factors. It is believed that approximately 125 mL to 150 mL of CSF is present in the human body at any one time, and approximately 500 mL of CSF is generated by the body each day. CSF circulates within the ventricular system of the brain. A majority of CSF is produced within the two lateral ventricles, from which CSF then passes through the interventricular foramina to the third ventricle and through the cerebral aqueduct to the fourth ventricle. From the fourth ventricle, CSF passes into the subarachnoid space through four openings: the central canal of the spinal cord, the median aperture, and the two lateral apertures. In this manner, CSF is present in the subarachnoid space, which covers the brain and the spinal cord and extends below the end of the spinal cord to the sacrum. Certain researchers believe that CSF moves in a single outward direction from the ventricles but multi-directionally within the subarachnoid space, with fluid movement being pulsatile and matching pressure waves generated in blood vessels by beating of the heart. Others contend that there is no unidirectional CSF circulation, but rather cardiac cycle-dependent bidirectional systolic-diastolic to-and-fro cranio-spinal movement of CSF. CSF returns to the vascular system by entering the dural venous sinuses via arachnoid granulations, which are outpouchings of the arachnoid mater into the venous sinuses around the brain. Such reabsorption of CSF occurs due to a pressure difference between the arachnoid mater and the venous sinuses. CSF is believed to turn over at a rate of approximately three to four times a day in the human body.

Certain researchers have speculated on causal relationships between abnormal CSF circulation and various neurological dysfunctions. With expanding knowledge in neuroscience, CSF physiology, and in particular ICP, has become an interesting target for treatment of chronic long-standing neurological pathologies, such as dementia, Alzheimer's disease, asymptomatic or minimally symptomatic Chiari malformation, cervical stenosis, headaches, epilepsy, sleep apnea, other sleep disorders, and even normal aging. In such cases, oscillations in ICP may be subtle and may occur only briefly in patients at unpredicted times of the day. Further, for a particular patient, ICP may be normal for a long period of time and may be altered intermittently when the patient engages in certain activities, such as driving or sleeping. An improved understanding of ICP and CSF circulation may allow clinicians to more easily identify neuronal damage and effectively treat certain neurological dysfunctions.

Various techniques and devices have been developed for measuring ICP for treatment of neurological pathologies. For example, external devices have been used for monitoring ICP for acute care of neurosurgical patients suffering from traumatic brain injury (TBI), meningitis, acute hydrocephalus, stroke, idiopathic intracranial hypertension, and other similar maladies. Use of such devices, however, presents a relatively high risk of infection, limits a practical period of monitoring, and restricts patient ambulation. Implantable ICP monitoring devices have been proposed to address these concerns. Although known implantable devices may be suitable for monitoring ICP of a patient in some circumstances, the use of such devices may suffer from certain problems. For example, certain ICP monitoring implants may measure and record data relating to ICP of a patient over time, while failing to account for other variables relating to CSF. As noted above, CSF circulation may depend on multiple factors, and thus data obtained from implantable devices that monitor only ICP may be misleading when analyzed in the absence of other variables. Further, the configurations of certain implantable ICP monitoring devices may limit placement of the devices within a patient. For example, certain devices may include a diaphragm or a sensor positioned at a distal end of the device and configured to facilitate measurement of ICP, with the device being intended for attachment within a hole formed in the skull of a patient. As a result, when such devices are implanted, placement of the diaphragm or the sensor may be limited to the epidural space or the subdural space, without an ability to monitor ICP in other regions of the brain. Additionally, such placement of the diaphragm or the sensor may result in certain complications, such as scar tissue formation causing deformation of or damage to the diaphragm or the sensor. Further, when known implantable devices are used for long-term ICP monitoring, batteries of the device may need to be recharged frequently via external devices, which may be cumbersome and time consuming for the patient.

Accordingly, there remains a need for improved devices and methods for monitoring properties of cerebrospinal fluid to facilitate diagnosis and/or treatment of various neurological pathologies.

SUMMARY OF THE DISCLOSURE

Various embodiments described herein provide implantable devices and related methods for monitoring properties of cerebrospinal fluid in a patient to facilitate diagnosis and/or treatment of a variety of neurological dysfunctions. As described below, the devices and methods may allow clinicians to easily and accurately identify abnormal CSF circulation in a manner that avoids the above-described problems associated with existing techniques for ICP monitoring.

According to one aspect, implantable devices for monitoring properties of cerebrospinal fluid of a patient are provided. In one embodiment, an implantable device may include a housing, a processor, a support member, one or more sensors, and a data storage. The housing may be configured for attaching to the patient. The processor may be disposed within the housing. The support member may extend from the housing, and at least a portion of the support member may be configured to move relative to the housing. The one or more sensors may be disposed outside of the housing and attached to the support member. The one or more sensors may be in operable communication with the processor and configured to detect one or more properties of cerebrospinal fluid. The data storage may be disposed within the housing and in operable communication with the processor, and the data storage may be configured to store cerebrospinal fluid data corresponding to the one or more properties.

In certain embodiments, the support member may include a flexible tube configured to bend relative to the housing. In certain embodiments, the support member may include a flexible wire configured to bend relative to the housing. In certain embodiments, the support member may include a proximal portion and a distal portion, with the proximal portion being fixedly attached to the housing, and the distal portion being configured to move relative to the housing. In certain embodiments, the one or more sensors may include a pressure sensor configured to detect a pressure of cerebrospinal fluid. In certain embodiments, the pressure sensor may include a fiber-optic sensor. In certain embodiments, the one or more sensors may include a flow sensor configured to detect a flow velocity of cerebrospinal fluid. In certain embodiments, the flow sensor may include a linear tube, a discoid member, or a thermometer. In certain embodiments, the one or more sensors may include a viscosity sensor configured to detect a viscosity of cerebrospinal fluid. In certain embodiments, the viscosity sensor may include a tube. In certain embodiments, the one or more sensors may include a biochemical sensor configured to detect one or more biomarkers of chronic neurological diseases. In certain embodiments, the biochemical sensor may be configured to detect beta-amyloid, tau-protein, alpha-synuclein and other molecules of interest. In certain embodiments, the one or more sensors may include a polsoxymetry sensor configured to detect oxygen saturation. In certain embodiments, the one or more sensors may include a Raman spectroscopy sensor configured to detect a molecular composition of cerebrospinal fluid. In certain embodiments, the one or more sensors may include one or more, all, or any combination of a pressure sensor, a flow sensor, a viscosity sensor, a biochemical sensor, a polsoxymetry sensor, and a Raman spectroscopy sensor.

In certain embodiments, the implantable device also may include a positional sensor in operable communication with the processor and configured to detect a positional orientation of the patient, and the data storage may be further configured to store positional data in association with the cerebrospinal fluid data. In certain embodiments, the positional sensor may include a gyroscope. In certain embodiments, the positional sensor may be disposed within the housing. In certain embodiments, the implantable device also may include a transceiver in operable communication with the processor and the data storage. The transceiver may be configured to transmit the cerebrospinal fluid data to an external device positioned outside of the patient.

In certain embodiments, the implantable device also may include a catheter in operable communication with a reservoir and a pump controlled by the processor and configured to administer a therapeutic agent or imaging agent, or to remove cerebrospinal fluid, in response to signals provided by an operator based on cerebrospinal fluid data collected and transmitted to the operator. In certain embodiments, the pump and reservoir may be disposed within the housing. In certain embodiments, the pump can deliver selected micrometered amounts of agents as desired for treatment or imaging based on the data collected.

In certain embodiments, the implantable device also may include a power storage device and a power generation device. The power storage device may be disposed within the housing and configured to power the processor and the one or more sensors. The power generation device may be configured to generate power based at least in part on at least one of: (i) cerebrospinal fluid flow within the patient; (ii) dural pulsations within the patient; (iii) vascular pulsations within the patient; and (iv) cranial movements of the patient.

In another embodiment, an implantable device may include a housing, a processor, a plurality of sensors, and a data storage. The housing may be configured for attaching to a patient. The processor may be disposed within the housing. The plurality of sensors may be disposed outside of the housing and configured to move relative to the housing, and the plurality of sensors may be in operable communication with the processor and configured to detect one or more properties of cerebrospinal fluid. The data storage may be disposed within the housing and in operable communication with the processor, and the data storage may be configured to store cerebrospinal fluid data corresponding to the one or more properties.

In certain embodiments, the plurality of sensors may include a pressure sensor configured to detect a pressure of cerebrospinal fluid. In certain embodiments, the plurality of sensors also may include at least one of: (i) a flow sensor configured to detect a flow velocity of cerebrospinal fluid; (ii) a viscosity sensor configured to detect a viscosity of cerebrospinal fluid; (iii) a biochemical sensor configured to detect one or more biomarkers of chronic neurological diseases; (iv) a polsoxymetry sensor configured to detect oxygen saturation; and (v) a Raman spectroscopy sensor configured to detect a molecular composition of cerebrospinal fluid. In certain embodiments, the plurality of sensors may include one or more, all, or any combination of a pressure sensor, a flow sensor, a viscosity sensor, a biochemical sensor, a polsoxymetry sensor, and a Raman spectroscopy sensor. In certain embodiments, the implantable device also may include a positional sensor fixed relative to the housing and in operable communication with the processor. The positional sensor may be configured to detect a positional orientation of the patient, and the data storage may be further configured to store positional data in association with the cerebrospinal fluid data.

In yet another embodiment, an implantable device may include a housing, a processor, a positional sensor, a pressure sensor, a flow sensor, and a data storage. The housing may be configured for attaching to a patient. The processor may be disposed within the housing. The positional sensor may be disposed within the housing and in operable communication with the processor, and the positional sensor may be configured to detect a positional orientation of the patient. The pressure sensor may be disposed outside of the housing and in operable communication with the processor, and the pressure sensor may be configured to detect a pressure of cerebrospinal fluid. The flow sensor may be disposed outside of the housing and in operable communication with the processor, and the flow sensor may be configured to detect a flow velocity of cerebrospinal fluid. The data storage may be disposed within the housing and in operable communication with the processor, and the data storage may be configured to store positional data based on signals generated by the positional sensor, pressure data based on signals generated by the pressure sensor, and flow velocity data based on signals generated by the flow sensor.

In certain embodiments, the implantable device also may include a viscosity sensor, a biochemical sensor, a polsoxymetry sensor, and a Raman spectroscopy sensor. The viscosity sensor may be disposed outside of the housing and in operable communication with the processor, and the viscosity sensor may be configured to detect a viscosity of cerebrospinal fluid. The biochemical sensor may be disposed outside of the housing and in operable communication with the processor, and the biochemical sensor may be configured to detect one or more biomarkers of chronic neurological diseases. The polsoxymetry sensor may be disposed outside of the housing and in operable communication with the processor, and the polsoxymetry sensor may be configured to detect oxygen saturation. The Raman spectroscopy sensor may be disposed outside of the housing and in operable communication with the processor, and the Raman spectroscopy sensor may be configured to detect a molecular composition of cerebrospinal fluid.

In still another embodiment, an implantable device may include a housing, a processor, one or more sensors, a data storage, and a power generation device. The housing may be configured for attaching to a patient. The processor may be disposed within the housing. The one or more sensors may be disposed outside of the housing and in operable communication with the processor, and the one or more sensors may be configured to detect one or more properties of cerebrospinal fluid. The data storage may be disposed within the housing and in operable communication with the processor, and the data storage may be configured to store cerebrospinal fluid data corresponding to the one or more properties. The power generation device may be attached to the housing and configured to generate power for powering the processor and the one or more sensors.

In certain embodiments, the power generation device may be configured to generate power based at least in part on at least one of: (i) cerebrospinal fluid flow within the patient; (ii) dural pulsations within the patient; (iii) vascular pulsations within the patient; and (iv) cranial movements of the patient. In certain embodiments, the implantable device also may include a power storage device in operable communication with the processor, the one or more sensors, and the power generation device, and the power generation device may be further configured to generate power for charging the power storage device.

According to another aspect, methods for implanting a device for monitoring properties of cerebrospinal fluid and treating a patient are provided. In one embodiment, a method for implanting a device for monitoring properties of cerebrospinal fluid of a patient may include attaching a housing of the device to the patient, moving at least a portion of a support member of the device relative to the housing, the support member extending from the housing, and positioning one or more sensors or catheters of the device within a target region of the patient, the one or more sensors configured to detect one or more properties of cerebrospinal fluid, and the one or more catheters configured to deliver therapeutic agents or imaging agents to the cerebrospinal fluid or to remove cerebrospinal fluid.

In certain embodiments, attaching the housing to the patient may include positioning the housing at least partially within a hole formed in a cranium of the patient, and attaching the housing to the cranium. In certain embodiments, attaching the housing to the patient may include positioning the housing at least partially within a hole formed in a spine of the patient, and attaching the housing to the spine. In certain embodiments, the support member may be flexible, and moving the at least a portion of the support member relative to the housing may include bending the at least a portion of the support member. In certain embodiments, positioning the one or more sensors or catheters within the target region may include positioning the one or more sensors or catheters within an epidural space of the patient. In certain embodiments, positioning the one or more sensors or catheters within the target region may include positioning the one or more sensors or catheters within a subdural space of the patient. In certain embodiments, positioning the one or more sensors or catheters within the target region may include positioning the one or more sensors or catheters within a subarachnoid space of the patient. In certain embodiments, positioning the one or more sensors or catheters within the target region may include positioning the one or more sensors or catheters within parenchymal tissue of a brain of the patient. In certain embodiments, positioning the one or more sensors or catheters within the target region may include positioning the one or more sensors or catheters within a ventricle of a brain of the patient.

In certain embodiments, the one or more sensors may include a pressure sensor configured to detect a pressure of cerebrospinal fluid, a flow sensor configured to detect a flow velocity of cerebrospinal fluid, and at least one of: (i) a viscosity sensor configured to detect a viscosity of cerebrospinal fluid; (ii) a biochemical sensor configured to detect one or more biomarkers of chronic neurological diseases; (iii) a polsoxymetry sensor configured to detect oxygen saturation; and (iv) a Raman spectroscopy sensor configured to detect a molecular composition of cerebrospinal fluid.

According to yet another aspect, methods for monitoring properties of cerebrospinal fluid of a patient are provided. In one embodiment, a method for monitoring properties of cerebrospinal fluid of a patient may include implanting a monitoring device within the patient. The monitoring device may include a housing, a processor, a plurality of sensors, and a data storage. The processor may be disposed within the housing. The plurality of sensors may be disposed outside of the housing and configured to move relative to the housing, and the plurality of sensors may be in operable communication with the processor. The data storage may be disposed within the housing and in operable communication with the processor. The method also may include detecting, by the plurality of sensors, one or more properties of cerebrospinal fluid of the patient, and storing, at the data storage, cerebrospinal fluid data corresponding to the one or more properties.

In certain embodiments, implanting the monitoring device within the patient may include attaching the housing to a cranium of the patient or a spine of the patient. In certain embodiments, implanting the monitoring device within the patient may include moving the plurality of sensors relative to the housing, and positioning the plurality of sensors within a target region of the patient. In certain embodiments, positioning the plurality of sensors within the target region may include: (i) positioning the plurality of sensors within an epidural space of the patient; (ii) positioning the plurality of sensors within a subdural space of the patient; (iii) positioning the plurality of sensors within a subarachnoid space of the patient; (iv) positioning the plurality of sensors within parenchymal tissue of a brain of the patient; or (v) positioning the plurality of sensors within a ventricle of the brain of the patient. In certain embodiments, the monitoring device also may include a positional sensor disposed within the housing and in operable communication with the processor, and the method further may include detecting, by the positional sensor, a positional orientation of the patient, and storing, at the data storage, positional data in association with the cerebrospinal fluid data.

In another embodiment, a method for monitoring properties of cerebrospinal fluid of a patient may include implanting a monitoring device within the patient. The monitoring device may include a housing, a processor, one or more sensors, catheters, a data storage, and a power generation device. The processor may be disposed within the housing. The one or more sensors or catheters may be disposed outside of the housing and in operable communication with the processor. The data storage may be disposed within the housing and in operable communication with the processor. The power generation device may be attached to the housing and in operable communication with the processor and the one or more sensors and pumps in communication with the catheters. The method also may include generating, by the power generation device, power for powering the processor and the one or more sensors, detecting, by the one or more sensors, one or more properties of cerebrospinal fluid of the patient, and storing, at the data storage, cerebrospinal fluid data corresponding to the one or more properties.

In certain embodiments, implanting the monitoring device within the patient may include attaching the housing to a cranium of the patient or a spine of the patient. In certain embodiments, generating the power for powering the processor and the one or more sensors and pumps associated with the catheters may include generating the power based at least in part on at least one of: (i) cerebrospinal fluid flow within the patient; (ii) dural pulsations within the patient; (iii) vascular pulsations within the patient; and (iv) cranial movements of the patient. In certain embodiments, the monitoring device also may include a positional sensor disposed within the housing and in operable communication with the processor, and the method further may include generating, by the power generation device, power for powering the positional sensor, detecting, by the positional sensor, a positional orientation of the patient, and storing, at the data storage, positional data in association with the cerebrospinal fluid data. In certain embodiments, the monitoring device also may include a power storage device in operable communication with the processor, the one or more sensors, the one or more pumps in communication with the one or more catheters, and the power generation device, and the method further may include charging, by the power generation device, the power storage device, and powering, by the power storage device, the processor and the one or more sensors and pumps.

In yet another embodiment, a method for monitoring properties of cerebrospinal fluid of a patient may include implanting a first monitoring device at least partially within a cranium of the patient, and implanting a second monitoring device at least partially within a spine of the patient. The first monitoring device may include a first housing, a first processor, one or more first sensors, one or more catheters, and a first data storage. The first processor may be disposed within the first housing. The one or more first sensors or catheters may be disposed outside of the housing and in operable communication with the first processor. The first data storage may be disposed within the first housing and in operable communication with the first processor. The second monitoring device may include a second housing, a second processor, one or more second sensors, one or more catheters, and a second data storage. The second processor may be disposed within the second housing. The one or more second sensors or catheters may be disposed outside of the housing and in operable communication with the second processor. The second data storage may be disposed within the second housing and in operable communication with the second processor. The method also may include detecting, by the one or more first sensors, one or more first properties of cerebrospinal fluid within the cranium of the patient, storing, at the first data storage, first cerebrospinal fluid data corresponding to the one or more first properties, detecting, by the one or more second sensors, one or more second properties of cerebrospinal fluid within the spine of the patient, and storing, at the second data storage, second cerebrospinal fluid data corresponding to the one or more second properties. The method also may include administering by the one or more first catheters, one or more therapeutic agents or imaging agents to the cerebrospinal fluid within the cranium of the patient.

In certain embodiments, implanting the first monitoring device at least partially within the cranium of the patient may include positioning the one or more first sensors within the cranium, and implanting the second monitoring device at least partially within the spine of the patient may include positioning the one or more second sensors within the spine. In each anatomical location described for sensors, catheters may also be utilized as described for the delivery of therapeutic or imaging agents or the removal of cerebrospinal fluid. In certain embodiments, positioning the one or more first sensors (or catheters) within the cranium may include: (i) positioning the one or more first sensors within an epidural space of the cranium; (ii) positioning the one or more first sensors within a subdural space of the cranium; (iii) positioning the one or more first sensors within a subarachnoid space of the cranium; (iv) positioning the one or more first sensors within parenchymal tissue of a brain of the patient; or (v) positioning the one or more first sensors within a ventricle of the brain of the patient. In certain embodiments, positioning the one or more second sensors (or catheters) within the spine may include: (i) positioning the one or more second sensors within a subarachnoid space of the spine; or (ii) positioning the one or more second sensors within a central canal of the spine.

In certain embodiments, the one or more first sensors may include a first pressure sensor configured to detect a first pressure of cerebrospinal fluid within the cranium, and the one or more second sensors may include a second pressure sensor configured to detect a second pressure of cerebrospinal fluid within the spine. In certain embodiments, the one or more first sensors also may include at least one of: (i) a first flow sensor configured to detect a first flow velocity of cerebrospinal fluid within the cranium; (ii) a first viscosity sensor configured to detect a first viscosity of cerebrospinal fluid within the cranium; (iii) a first biochemical sensor configured to detect one or more biomarkers of chronic neurological diseases within the cranium; (iv) a first polsoxymetry sensor configured to detect oxygen saturation within the cranium; and (v) a first Raman spectroscopy sensor configured to detect a first molecular composition of cerebrospinal fluid within the cranium, and the one or more second sensors also may include at least one of: (i) a second flow sensor configured to detect a second flow velocity of cerebrospinal fluid within the spine; (ii) a second viscosity sensor configured to detect a second viscosity of cerebrospinal fluid within the spine; (iii) a second biochemical sensor configured to detect one or more biomarkers of chronic neurological diseases within the spine; (iv) a second polsoxymetry sensor configured to detect oxygen saturation within the spine; and (v) a second Raman spectroscopy sensor configured to detect a second molecular composition of cerebrospinal fluid within the spine.

In certain embodiments, the first monitoring device also may include a positional sensor fixed relative to the first housing and in operable communication with the first processor, and the method further may include detecting, by the positional sensor, a positional orientation of the patient, and storing, at the first data storage, positional data in association with the first cerebrospinal fluid data. In certain embodiments, the method further may include transmitting, by a first transceiver of the first monitoring device, the first cerebrospinal fluid data to an external device positioned outside of the patient, and transmitting, by a second transceiver of the second monitoring device, the second cerebrospinal fluid data to the external device. In certain embodiments, the method further may include comparing, by the external device, respective values of the first cerebrospinal fluid data and respective values of the second cerebrospinal fluid data, and identifying, by the external device, one or more differences between the respective values of the first cerebrospinal fluid data and respective values of the second cerebrospinal fluid data. In certain embodiments, the method further may include diagnosing the patient with one or more neurological pathologies based at least in part on at least one of: (i) the first cerebrospinal fluid data; (ii) the second cerebrospinal fluid data; and (iii) the one or more differences between the respective values of the first cerebrospinal fluid data and respective values of the second cerebrospinal fluid data.

According to other embodiments, implantable devices for monitoring and modifying properties of cerebrospinal fluid of a patient are provided. In one embodiment, an implantable device may include a housing, a processor, a support member, one or more sensors, one or more catheters, and a data storage. The housing may be configured for attaching to the patient. The processor may be disposed within the housing. The support member may extend from the housing, and at least a portion of the support member may be configured to move relative to the housing. The one or more sensors may be disposed outside of the housing and attached to the support member. The one or more sensors may be in operable communication with the processor and configured to detect one or more properties of cerebrospinal fluid. The one or more catheters may be disposed outside of the housing and attached to the support member. The one or more catheters have a proximal port and a distal port disposed outside of the housing, and a lumen extending therethrough, and may be attached to the support member or independently extend from the housing. The one or more catheters may be in operable communication with the processor via a pump and a reservoir and configured to administer to the cerebrospinal fluid various therapeutic agents (e.g., thrombolytic agents) or imaging agents (e.g., contrast dye), or to remove fluid (e.g. cerebrospinal fluid or blood) to relieve pressure. The data storage may be disposed within the housing and in operable communication with the processor, and the data storage may be configured to store or to send cerebrospinal fluid data corresponding to the one or more properties. Each catheter can be configured to automatically administer agents to the cerebrospinal fluid, or to remove biological fluid, by a pump and fluid reservoir attached proximally thereto, and activated by the processor in response to predefined monitoring criteria, or these functions can be activated remotely by command of the operator, or manually by the operator, including with a syringe attached proximally thereto, in response to monitoring of abnormalities by the sensor.

According to certain embodiments, the invention provides methods of treatment for a patient comprising monitoring one or more properties of the cerebrospinal fluid of the patient with an implantable device as described herein having a sensor, detecting a condition or abnormality, and administering a therapeutic agent, an imaging agent, and/or removing cerebrospinal fluid through a catheter in an amount effective to treat a condition or abnormality detected by the sensor. The one or more catheters used in conjunction with the sensors has a proximal port and a distal port disposed outside of the housing and a lumen extending therethrough, and may be attached to the support member. The one or more catheters may be connected at the proximal end to a reservoir and a pump in operable communication with the processor and configured to administer to the cerebrospinal fluid various therapeutic agents (e.g., thrombolytic agents) or imaging agents (e.g., contrast dye), or to remove fluid (e.g. cerebrospinal fluid or blood) to relieve pressure.

These and other aspects and embodiments of the present disclosure will be apparent or will become apparent to one of ordinary skill in the art upon review of the following detailed description when taken in conjunction with the several drawings and the appended claims.

BRIEF DESCRIPTION OF THE DRAWINGS

In describing the various embodiments of the present disclosure, reference is made to the accompanying drawings, which are not necessarily drawn to scale, and wherein:

FIG. 2A is a perspective view of an implantable device for monitoring properties of cerebrospinal fluid in accordance with one or more embodiments of the disclosure, showing a housing, a support member, and a plurality of sensors of the implantable device.

FIG. 2B is a perspective view of the implantable device of FIG. 2A, showing the housing, the support member, the sensors, and internal components of the implantable device.

FIG. 2C is an exploded perspective view of the implantable device of FIG. 2A, showing the support member, the sensors, a processor, a memory device, a data storage, a positional sensor, an analog-digital converter, an antenna, a transceiver, a power storage device, a charging device, a power generation device, and fasteners of the implantable device.

DETAILED DESCRIPTION OF THE DISCLOSURE

Figure 1A:
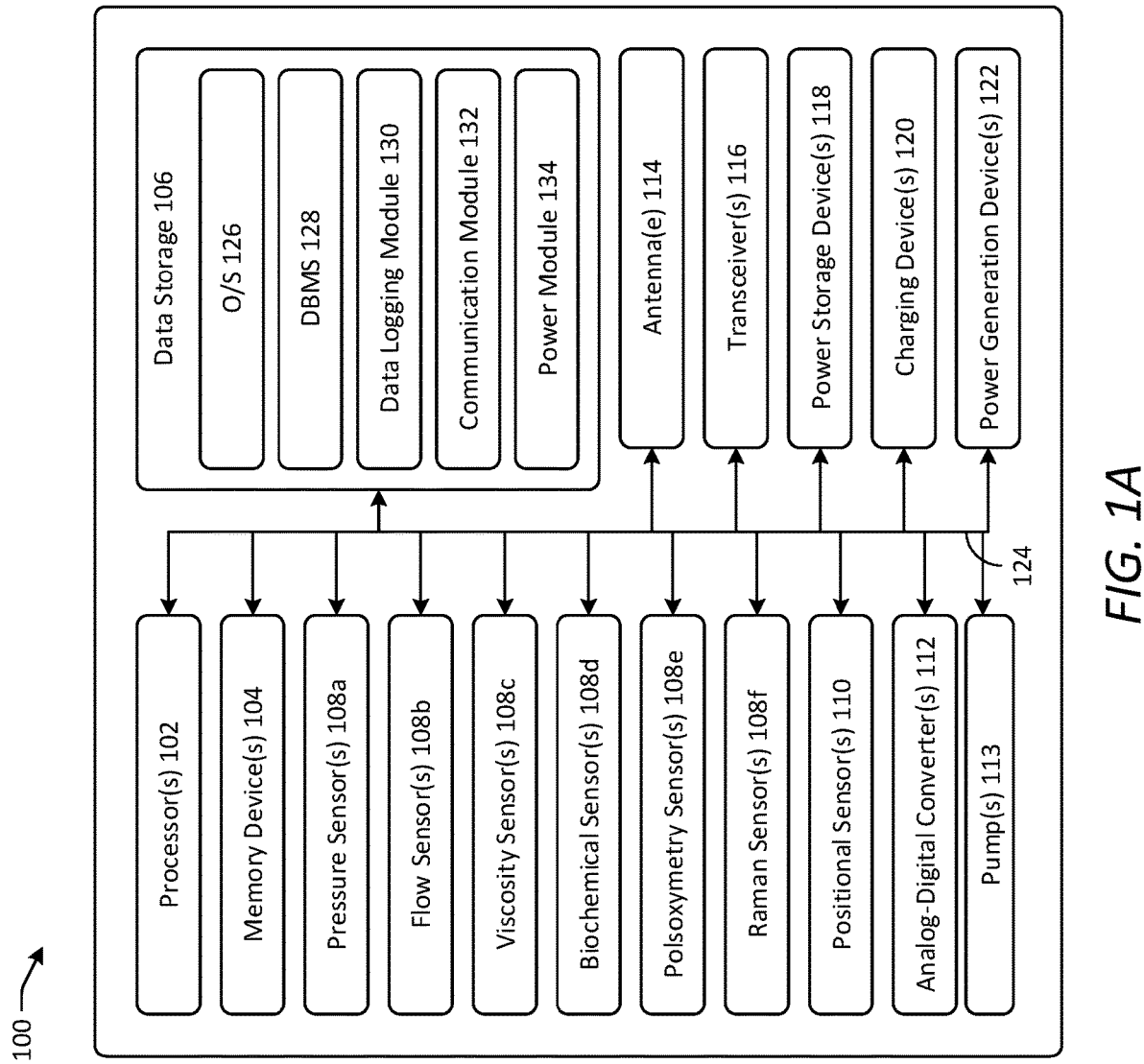
FIG. 1A is a schematic view of an implantable device for monitoring properties of cerebrospinal fluid in accordance with one or more embodiments of the disclosure.

Various embodiments of the present disclosure provide improved implantable devices and related methods for long-term monitoring of properties of cerebrospinal fluid in a patient to facilitate diagnosis and/or treatment of various neurological dysfunctions. Such devices and methods may address one or more of the above-described problems experienced with existing technology for ICP monitoring and identifying abnormal CSF circulation and treatment thereof. For example, as compared to known external ICP monitoring devices, the implantable devices described herein may decrease incidence of infection, allow for continuous ICP monitoring over an extended period of time, and allow patients to move freely and engage in normal activities throughout the monitoring period. As compared to existing implantable ICP monitoring devices, the implantable devices described herein may measure and record data for several relevant variables relating to CSF in addition to ICP. In this manner, the described devices and methods may provide clinicians and/or researchers with a rich data set for analyzing CSF circulation over time to more effectively identify and treat neurological pathologies. Additionally, the configurations of the implantable devices described herein may allow one or more sensors to be placed in various regions of the patient's brain. For example, the implantable devices may allow for epidural, subdural, intraparenchymal, and/or intraventricular placement of the one or more sensors, as may be desired by clinicians in different circumstances. Further, the implantable devices may allow the one or more sensors to be placed in a manner that inhibits deformation of or damage to the sensors due to scar tissue formation. Further, the implantable devices may allow remote communication of the CSF data and control of responsive treatment through automated injection of a therapeutic agent or a contrast agent or removal of CSF via a catheter in operable communication with a reservoir and pump. Finally, as described below, the implantable devices described herein may provide various means for powering the device over a long monitoring period, reducing or eliminating the need for use of an external device to recharge batteries of the implanted device. In this manner, embodiments of the present disclosure may provide significant improvements over existing devices and methods for CSF monitoring.

Embodiments of the present disclosure are described herein below with reference to the accompanying drawings, in which some, but not all, embodiments are shown. Indeed, the devices and methods disclosed may be embodied in many different forms and should not be construed as limited to the embodiments set forth herein; rather, these embodiments are provided so that this disclosure is thorough and complete and fully conveys the scope of the devices and methods to those skilled in the art. Like reference numbers refer to like elements throughout. The singular forms "a," "an," and "the" can refer to plural instances unless the context clearly dictates otherwise or unless explicitly stated.

Earlier observers have speculated on the causal relationships between abnormal CSF circulation and a variety of neurological dysfunctions. Such speculations have been at least partially validated by recent evidence and inquiries contravening the traditional static viewpoint of CSF circulation. Contemporary inquiries establish a number of factors that influence both CSF production and CSF absorption (e.g., sleep disturbance, neck position, cerebral metabolism, brain atrophy, medications, etc.). Thus, transient periods of abnormality are possibly mingled with periods of normality. Such episodic alterations suggest that the physiological arrangements that underpin CSF circulation may be in some ways likened to blood pressure alterations, in that long-standing CSF abnormalities may be both unappreciated and gradual, though virulent enough to cause substantial neurological injury. The present inventors suggest that cervical stenosis (blocking an important CSF decompressive pathway into the vertebral canal) is among the largely unappreciated causes of abnormal CSF circulation and may play a role in cephalad neuronal dysfunction. Such a blockage is correlated with age and easily assessed by cine MRI study. Indeed, episodic disturbances can diminish CSF cerebral flow circulation, increasing deposition in cerebral parenchyma of contrary metabolic products (e.g., beta Amyloid), and possibly having a causal influence on senile dementia. Additionally, cervical stenosis, by increasing posterior fossa cerebral pressure, could play a causal role in a number of afflictions, such as sleep apnea, concomitant respiratory and circulatory dysfunction, hypertension, chronic occipital headaches, tinnitus, and other conditions.

The present inventors further suggest that, among those patients with substantial cervical stenosis (extensive enough to block CSF circulation in the cervical area as identified by cine MRI), appropriate comparative clinical studies could be undertaken to demarcate associations with pre-senile dementia, sleep disturbance, and posterior fossa dysfunction. It is also suggested that an intracranial monitoring implant for chronically monitoring both intracranial pressure and CSF flow—a monitoring device comparable to the rather less invasive sphygmometric evaluation of blood pressure—would be particularly advantageous. If such speculations prove correct, different therapeutic regimens that may improve outcome can be provided. For example, better sleep hygiene (to, by position, maximize CSF flow) and possibly more aggressive operative decompressive intervention may be implemented to diminish cervical obstruction.

It is important to understand that CSF flow is not a constant steady stream, and, contrary to traditional thinking, CSF is not exclusively produced by the choroid plexus. CSF production changes with age and changes throughout the day. Additionally, CSF flow alterations may be transient, variable, and positional, and thus intracranial pressure is variable. See T. Brinker, E. Stopa, J. Morrison and P. Klinge, A new look at cerebrospinal fluid circulation, *Fluids and Barriers of the CNS* 11 (2014), p. 10. CSF circulation arrangements are quite complicated. They involve the blood-brain barrier, choroid plexus barrier, glia limitans, ependyma, pia mater, as well as transcellular fluid movements. In general, CSF is produced in the brain as well as in the choroid plexus. There is an extensive internal circulation between the cells and extracellular fluid, which then makes its way into the blood stream. See id. The basic principles to consider in these fluid movements are diffusion, bulk flow or convection, substantial amount of filtration and secretion, and active transport requiring energies, which is particularly true when CSF is secreted from the chorionic plexus into the ventricular system. See S. B. Hladky and M. A. Barrand, Mechanisms of fluid movement into, through and out of the brain: evaluation of the evidence, *Fluids and Barriers of the CNS* 11 (2014), p. 26.

CSF flow abnormalities may be transient and may depend upon secondary factors. CSF circulation comprises not only a dedicated flow of CSF but also a pulsatile to-and-fro movement throughout the entire brain, with local fluid exchange between blood, interstitial fluid and CSF, astrocytes, aquaporins, and other membrane transporters as the key element in the brain water and CSF homeostasis. See T. Brinker, E. Stopa, J. Morrison and P. Klinge, A new look at cerebrospinal fluid circulation, *Fluids and Barriers of the CNS* 11 (2014), p. 10. In considering these flow arrangements, it should be remembered that positioning also may affect CSF flow. See A. E. Bond, J. A. Jane, Sr., K. C. Liu and E. H. Oldfield, Changes in cerebrospinal fluid flow assessed using intraoperative MRI during posterior fossa decompression for Chiari malformation, *J Neurosurg* 122 (2015), pp. 1068-1075. As an example, positional CSF flow obstruction could serve Chiari I malformation where there is a significant CSF flow improvement in the prone position when assessed using intraoperative phase-contrast MRI techniques. See id.

Numerous papers have explored the role of the spinal canal in CSF circulation. At least one observer noted that the spinal contribution to CSF pressure in cats was substantial, particularly after applying Mannitol. See M. Klarica, R. Varda, M. Vukic, D. Oreskovic, M. Rados and M. Bulat, Spinal contribution to CSF pressure lowering effect of mannitol in cats, *Acta Neurochir* Suppl 95 (2005), pp. 407-410. It is well known that CSF circulation also depends upon the spinal arachnoid villae and the lymphatic systems of the cranial nerves. Because there are many more spinal nerves than cranial nerves, one would imagine that the spinal nerves are playing a major role. See L. Sakka, G. Coll and J. Chazal, Anatomy and physiology of cerebrospinal fluid, *Eur Ann Otorhinolaryngol Head Neck Dis* 128 (2011), pp. 309-316. In looking at the respective volumes of CSF, it appears that the amount of CSF in the spinal subarachnoid space is approximately 25 mL, which is about 16% of total CSF volume. See id.

The extraordinary complexity of the human body often defeats casual inquiry. A constellation of feedback mechanisms maintains the homeostatic structure of our physical well-being. This is particularly true with CSF circulation. An intrinsic feedback mechanism maintains CSF production and absorption at an optimal level. That such a mechanism exists is obvious for any casual inquiry. However, the particulars of how this mechanism is structured are not well known. Some of the factors obscuring CSF flow include obstruction, venous outflow difficulties, cervical stenosis, and indeed Chiari malformations. Additionally, in the presence of increased CSF viscosity, outflow arrangements can be compromised. Such changes in viscosity can be increased as a sequel to Subarachnoid Hemorrhage or meningitis infection, including viral meningitis. When such obstructions occur, the CSF outflow pattern increases through a non-blocked pathway.

Understanding the CSF circulation and instituting an appropriate therapeutic intervention promises important improvements in neuronal function. Because there is no clear understanding about the transitory nature of CSF alterations, a manometer for ICP is needed. Once a marker is obtained, steps to improve CSF circulation can be taken. For example, for patients with cervical stenosis, better sleep posture, use of a collar, or sleeping in an upright position may be suggested. Prophylactic shunting or decompressions also may be suggested more aggressively. To understand CSF circulation better, longer follow-up and improved clinical studies are needed. Improved litmus papers to detect CSF circulation abnormalities also are needed. The present inventors propose the use of an implantable device, embodiments of which are described in detail herein, in patients who have had some intracerebral injury that warrants implantation of the device. After the patient is over the acute problem, the implanted device can remain to pick up intracranial data that can be harvested over a long period of time with appropriate monitoring arrangements and data collection.

Obvious CSF flow obstruction is a well-established acute and subacute cause of dementia. Unfortunately, the less-obvious vagaries of CSF production and absorption remain relatively unexplored and, logically, could play a role in neuronal destruction. There remains a need to demarcate processes (particularly cervical stenosis) by which restricted (often episodic) CSF circulation subtly damages neuronal tissue, and to develop studies and arrangements to track and prevent the onset of such difficulties. To assess the impact of recent new understandings of CSF flow dynamics, and on the possible etiology of dementia, a substantial literature review was conducted. The literature review suggests the elevated prevalence of cervical stenosis, concomitant CSF flow obstruction and dementia, in an elderly population. The literature further suggests that cervical stenosis can significantly, and often discreetly, compromise CSF circulation, thereby injuring neuronal tissue by direct untoward pressure, by restriction of cerebral CSF bulk flow retarding beta-amyloid clearance, and by ventricular ependymal cell damage allowing trans-ependymal CSF flow neuronal damage. Moreover, such restriction could contribute to the development of sleep apnea, thereby causing concomitant respiratory and circulatory dysfunction, promoting the development of a vicious cycle in which widespread direct neuronal injury as well as further increase in ICP occurs. The present inventors conclude that, among other obstructive possibilities, cervical stenosis could play a role in the development of dementia. Recognition of subtle, chronic CSF alterations (in some ways comparable to chronically abnormal blood pressure) calls for the development of technology to measure CSF circulation on a 24-hour basis. If the parameters of episodic abnormalities could be better adjudicated, prevention of such events could reasonably be effectuated by cervical decompression, therapeutic drug regimen, and altered sleep position.

Referring now to the drawings, FIG. 1A schematically illustrates an example implantable device 100 (which also may be referred to as a "CSF monitoring device," a "monitoring device," an "implant," or a "device") according to one or more embodiments of the disclosure. As described below, the implantable device 100 may be configured for implantation within a patient to monitor one or more properties of cerebrospinal fluid (CSF) of a patient over an extended period of time. In some instances, the device 100 may be implanted in the cranium of a patient to monitor properties of CSF therein. In some instances, the device 100 may be implanted in the spine of a patient to monitor properties of CSF therein. In some instances, multiple devices 100 may be implanted in a patient, with a combination of cranial and spinal implantation of the devices 100. As described in detail below, the implantable device 100 may include one or more sensors for detecting properties of CSF, data storage for logging CSF data indicative of the detected properties, and communication components for transmitting the CSF data to and receiving other data from an external device 140. The CSF data may be processed by the implantable device 100 and/or the external device 140 and then analyzed by a clinician or a researcher to facilitate diagnosis and/or treatment of various neurological dysfunctions. In some embodiments, the implantable device 100 may include one or more power storage devices for powering the sensors, the communication components, pumps, and/or other components of the device 100. In some embodiments, the power storage devices may be rechargeable via the external device 140. In some embodiments, the implantable device 100 may include one or more power generation devices for powering components of the device 100 and/or charging the power storage devices.

The implantable device 100 may allow for long-term monitoring of properties of CSF in a patient to facilitate diagnosis and/or treatment of a variety of neurological pathologies. As described in detail below, the implantable device 100 and methods for its use may address one or more of the above-described problems experienced with existing technology for ICP monitoring and identifying abnormal CSF circulation. For example, as compared to existing implantable ICP monitoring devices, the implantable device 100 advantageously may measure and record data for several relevant variables relating to CSF in addition to ICP. In this manner, the device 100 may provide clinicians and/or researchers with a rich data set for analyzing CSF circulation over time to more effectively identify and treat neurological pathologies. Additionally, the implantable device 100 may be configured in a manner that allows the sensors thereof to be placed in various regions of the patient's brain. For example, the implantable device 100 may allow for epidural, subdural, intraparenchymal, and/or intraventricular placement of the sensors, as may be desired by clinicians in different circumstances. Further, the implantable device 100 may be configured to allow the sensors to be placed in a manner that inhibits deformation of or damage to the sensors due to scar tissue formation. Finally, the implantable device 100 may include various means for powering the device 100 over a long monitoring period, reducing or eliminating the need for use of the external device 140 to recharge batteries of the implanted device 100 in certain scenarios. In this manner, embodiments of the implantable device 100 and its use may provide significant improvements over existing devices and methods for CSF monitoring.

As shown in FIG. 1A, the implantable device 100 may include one or more processor(s) 102 (which also may be referred to as a "processing unit"), one or more memory device(s) 104 (which also may be referred to as "memory"), a data storage 106, one or more cerebrospinal fluid (CSF) sensor(s) 108 (which also may be referred to as a "CSF property sensor"), one or more positional sensor(s) 110 (which also may be referred to as a "positional orientation sensor" or an "orientation sensor"), one or more analog-digital converter(s) 112, one or more antenna(e) 114, one or more transceiver(s) 116, one or more power storage device(s) 118, one or more charging device(s) 120, and one or more power generation device(s) 122. The implantable device 100 also may include one or more bus(es) 124 that functionally couple various components of the implantable device 100 for communication between the components. These components of the implantable device 100 and their functions are described in detail below. It will be appreciated that the implantable device 100 illustrated in FIG. 1A is merely one example of the device 100 described herein, and that various configurations of the device 100 may be used. In some embodiments, certain components illustrated in FIG. 1A may be omitted from the device 100, and, in other embodiments, additional components not illustrated in FIG. 1A may be included in the device 100. The following description may refer to the aforementioned components of the implantable device 100 in singular form for simplicity, although it will be appreciated that multiple instances of such components may be present in certain embodiments of the device 100.

The bus(es) 124 may include at least one of a system bus, a memory bus, an address bus, or a message bus, and may permit the exchange of information (e.g., data (including computer-executable code), signaling, etc.) between various components of the implantable device 100. The bus(es) 124 may include, without limitation, a memory bus or a memory controller, a peripheral bus, an accelerated graphics port, and so forth. The bus(es) 124 may be associated with any suitable bus architecture including, without limitation, an Industry Standard Architecture (ISA), a Micro Channel Architecture (MCA), an Enhanced ISA (EISA), a Video Electronics Standards Association (VESA) architecture, an Accelerated Graphics Port (AGP) architecture, a Peripheral Component Interconnects (PCI) architecture, a PCI-Express architecture, a Personal Computer Memory Card International Association (PCMCIA) architecture, a Universal Serial Bus (USB) architecture, and so forth.

The memory device 104 of the implantable device 100 may include volatile memory (memory that maintains its state when supplied with power), such as random access memory (RAM), and/or non-volatile memory (memory that maintains its state even when not supplied with power), such as read-only memory (ROM), flash memory, ferroelectric RAM (FRAM), and so forth. Persistent data storage, as that term is used herein, may include non-volatile memory. In certain example embodiments, volatile memory may enable faster read/write access than non-volatile memory. However, in certain other example embodiments, certain types of non-volatile memory (e.g., FRAM) may enable faster read/write access than certain types of volatile memory.

In various implementations, the memory device 104 may include multiple different types of memory such as various types of static random access memory (SRAM), various types of dynamic random access memory (DRAM), various types of unalterable ROM, and/or writeable variants of ROM such as electrically erasable programmable read-only memory (EEPROM), flash memory, and so forth. The memory device 104 may include main memory as well as various forms of cache memory such as instruction cache(s), data cache(s), translation lookaside buffer(s) (TLBs), and so forth. Further, cache memory such as a data cache may be a multi-level cache organized as a hierarchy of one or more cache levels (L1, L2, etc.).

The data storage 106 may include removable storage and/or non-removable storage including, but not limited to, magnetic storage, optical disk storage, and/or tape storage. The data storage 106 may provide non-volatile storage of computer-executable instructions and other data. The memory device 104 and the data storage 106, removable and/or non-removable, are examples of computer-readable storage media (CRSM) as that term is used herein.

The data storage 106 may store computer-executable code, instructions, or the like that may be loadable into the memory device 104 and executable by the processor(s) 102 to cause the processor(s) 102 to perform or initiate various operations described herein. The data storage 106 may additionally store data that may be copied to the memory device 104 for use by the processor(s) 102 during the execution of the computer-executable instructions. Moreover, output data generated as a result of execution of the computer-executable instructions by the processor(s) 102 may be stored initially in the memory device 104, and may ultimately be copied to data storage 106 for non-volatile storage.

More specifically, the data storage 106 may store one or more operating systems (O/S) 126; one or more database management systems (DBMS) 128; and one or more program module(s), applications, engines, computer-executable code, scripts, or the like such as, for example, one or more data logging module(s) 130, one or more communication module(s) 132 and/or one or more power module(s) 134. Some or all of these module(s) may be or include sub-module(s). Any of the components depicted as being stored in the data storage 106 may include any combination of software, firmware, and/or hardware. The software and/or firmware may include computer-executable code, instructions, or the like that may be loaded into the memory device 104 for execution by one or more of the processor(s) 102. Any of the components depicted as being stored in the data storage 106 may support the functionality described in reference to the corresponding components named in this disclosure.

The data storage 106 may further store various types of data utilized by the components of the implantable device 100. Any data stored in the data storage 106 may be loaded into the memory device 104 for use by the processor(s) 102 in executing computer-executable code. In addition, any data depicted as being stored in the data storage 106 may potentially be stored in one or more datastore(s) and may be accessed via the DBMS 128 and loaded in the memory device 104 for use by the processor(s) 102 in executing computer-executable code. The datastore(s) may include, but are not limited to, databases (e.g., relational, object-oriented, etc.), file systems, flat files, distributed datastores in which data is stored on more than one node of a computer network, peer-to-peer network datastores, or the like.

The processor(s) 102 may be configured to access the memory device 104 and execute computer-executable instructions loaded therein. For example, the processor(s) 102 may be configured to execute computer-executable instructions of the various program module(s), applications, engines, or the like of the implantable device 100 to cause or facilitate various operations to be performed in accordance with one or more embodiments of the disclosure. The processor(s) 102 may include any suitable processing unit capable of accepting data as input, processing the input data in accordance with stored computer-executable instructions, and generating output data. The processor(s) 102 may include any type of suitable processing unit including, but not limited to, a central processing unit, a microprocessor, a Reduced Instruction Set Computer (RISC) microprocessor, a Complex Instruction Set Computer (CISC) microprocessor, a microcontroller, an Application Specific Integrated Circuit (ASIC), a Field-Programmable Gate Array (FPGA), a System-on-a-Chip (SoC), a digital signal processor (DSP), and so forth. Further, the processor(s) 102 may have any suitable microarchitecture design that includes any number of constituent components such as, for example, registers, multiplexers, arithmetic logic units, cache controllers for controlling read/write operations to cache memory, branch predictors, or the like. The microarchitecture design of the processor(s) 102 may be capable of supporting any of a variety of instruction sets.

As shown in FIG. 1A, the implantable device 100 may include a plurality of the CSF sensors 108 each configured to detect one or more properties of CSF. According to the illustrated embodiment, the implantable device 100 may include one or more pressure sensor(s) 108a, one or more flow sensor(s) 108b, one or more viscosity sensor(s) 108c, one or more biochemical sensor(s) 108d, one or more polysoxymetry sensor(s) 108e, and one or more Raman spectroscopy sensor(s) 108f. Any combination of such sensors 108 may be used in the implantable device 100 in various embodiments. Further, the plurality of sensors 108 may include other types of sensors for detecting additional properties of CSF that may be relevant to analyzing CSF circulation in a patient, diagnosing one or more neurological dysfunctions, and/or treating one or more neurological dysfunctions. In some embodiments, the sensors 108 may be formed of radiopaque materials, or may include markers formed of radiopaque materials, to assist a clinician in visualizing positions of the sensors 108 during implantation of the device 100.

The pressure sensor 108a may be configured to detect a pressure of CSF within a region of a patient in which the pressure sensor 108a is positioned. For example, the pressure sensor 108a may be positioned within the cranium of a patient, and thus the pressure sensor 108a may detect a pressure of CSF within the cranium (i.e., ICP). As another example, the pressure sensor 108a may be positioned within the spine of a patient, and thus the pressure sensor 108a may detect a pressure of CSF within the spine. In some embodiments, the pressure sensor 108a may include, or may be, a fiber-optic sensor, although other suitable types of sensors for detecting a pressure of CSF may be used for the pressure sensor 108a. The pressure sensor 108a may be configured to detect a pressure of CSF and generate a signal corresponding to the detected pressure. In some embodiments, the signal generated by the pressure sensor 108a may be an analog signal, which may be transmitted to the analog-digital converter 112 for conversion to a digital signal. In some embodiments, the signal generated by the pressure sensor 108a may be a digital signal. The digital signal corresponding to the detected pressure may be received by the processor(s) 102, which may direct storage of corresponding pressure data at the data storage 106. In some embodiments, the pressure data may include numerical data (i.e., numerical values) indicative of the detected pressure, although other forms of the pressure data may be used. Detection of CSF pressure and storage of the pressure data at the data storage 106 may be carried out as directed by the data logging module 130.

The flow sensor 108b may be configured to detect a flow velocity of CSF within a region of a patient in which the flow sensor 108b is positioned. For example, the flow sensor 108b may be positioned within the cranium of a patient, and thus the flow sensor 108b may detect a flow velocity of CSF within the cranium. As another example, the flow sensor 108b may be positioned within the spine of a patient, and thus the flow sensor 108b may detect a flow velocity of CSF within the spine. In some embodiments, the flow sensor 108b may include a hollow linear tube or a discoid member, although other suitable configurations of the flow sensor 108b may be used. In some embodiments, the flow sensor 108b may be, or may include, a propelling sensor, a thermometer, a pair of fiber optic sensors spaced apart from one another, or other suitable components for detecting a flow velocity of CSF. In some embodiments, the flow sensor 108b may be configured to detect a flow velocity of CSF regardless of a flow direction of the CSF. The flow sensor 108b may be configured to detect a flow velocity of CSF and generate a signal corresponding to the detected flow velocity. In some embodiments, the signal generated by the flow sensor 108b may be an analog signal, which may be transmitted to the analog-digital converter 112 for conversion to a digital signal. In some embodiments, the signal generated by the flow sensor 108b may be a digital signal. The digital signal corresponding to the detected flow velocity may be received by the processor(s) 102, which may direct storage of corresponding flow velocity data at the data storage 106. In some embodiments, the flow velocity data may include numerical data (i.e., numerical values) indicative of the detected flow velocity, although other forms of the flow velocity data may be used. Detection of CSF flow velocity and storage of the flow velocity data at the data storage 106 may be carried out as directed by the data logging module 130.

The viscosity sensor 108c may be configured to detect a viscosity of CSF within a region of a patient in which the viscosity sensor 108c is positioned. For example, the viscosity sensor 108c may be positioned within the cranium of a patient, and thus the viscosity sensor 108c may detect a viscosity of CSF within the cranium. As another example, the viscosity sensor 108c may be positioned within the spine of a patient, and thus the viscosity sensor 108c may detect a viscosity of CSF within the spine. In some embodiments, the viscosity sensor 108c may include a hollow tube, although other suitable configurations of the viscosity sensor 108c may be used. In some embodiments, the viscosity sensor 108c may be, or may include, an inline viscometer, a solid-state viscometer, a piezoelectric sensor, a surface acoustic wave sensor, or other suitable components for detecting a viscosity of CSF. The viscosity sensor 108c may be configured to detect a viscosity of CSF and generate a signal corresponding to the detected viscosity. In some embodiments, the signal generated by the viscosity sensor 108c may be an analog signal, which may be transmitted to the analog-digital converter 112 for conversion to a digital signal. In some embodiments, the signal generated by the viscosity sensor 108c may be a digital signal. The digital signal corresponding to the detected viscosity may be received by the processor(s) 102, which may direct storage of corresponding viscosity data at the data storage 106. In some embodiments, the viscosity data may include numerical data (i.e., numerical values) indicative of the detected viscosity, although other forms of the viscosity data may be used. Detection of CSF viscosity and storage of the viscosity data at the data storage 106 may be carried out as directed by the data logging module 130.

The biochemical sensor 108d may be configured to detect one or more biomarkers of chronic neurological diseases within a region of a patient in which the biochemical sensor 108d is positioned. For example, the biochemical sensor 108d may be positioned within the cranium of a patient, and thus the biochemical sensor 108d may detect one or more biomarkers present within the cranium. As another example, the biochemical sensor 108d may be positioned within the spine of a patient, and thus the biochemical sensor 108d may detect one or more biomarkers present within the spine. Example biomarkers that may be detected by the biochemical sensor 108d may include beta-amyloid, tau protein and alpha-synuclein, although the biochemical sensor 108d may be configured to detect various types of biomarkers indicative of chronic neurological diseases. In some embodiments, the biochemical sensor 108d also may be configured to detect biomarkers of acute neurological conditions or other neurologically active substances within a region of a patient in which the biochemical sensor 108d is positioned. Example biomarkers that may be detected by the biochemical sensor 108d may include electrolytes, glucose, enzymes, bacterial or viral DNA or RNA, hormones, lactic acid, and melatonin, although the biochemical sensor 108d may be configured to detect various types of biomarkers indicative of acute neurological conditions. In some embodiments, the biochemical sensor 108d may be, or may include, a conductimetric sensor, a potentiometric sensor, an amperometric sensor, a calorimetric sensor, a gravimetric sensor, a coulometric sensor, or other suitable components for detecting a biochemical. The biochemical sensor 108d may be configured to detect one or more biomarkers and generate a signal corresponding to the detected biochemical. In some embodiments, the signal generated by the biochemical sensor 108d may be an analog signal, which may be transmitted to the analog-digital converter 112 for conversion to a digital signal. In some embodiments, the signal generated by the biochemical sensor 108d may be a digital signal. The digital signal corresponding to the detected biochemical may be received by the processor(s) 102, which may direct storage of corresponding biochemical data at the data storage 106. In some embodiments, the biochemical data may include numerical data (i.e., numerical values) indicative of the detected biochemical and/or a concentration of the detected biochemical, although other forms of the biochemical data may be used. Detection of biomarkers and storage of the biochemical data at the data storage 106 may be carried out as directed by the data logging module 130.

The polysoxymetry sensor 108e may be configured to detect oxygen saturation of CSF within a region of a patient in which the polysoxymetry sensor 108e is positioned. For example, the polysoxymetry sensor 108e may be positioned within the cranium of a patient, and thus the polysoxymetry sensor 108e may detect oxygen saturation of CSF within the cranium. As another example, the polysoxymetry sensor 108e may be positioned within the spine of a patient, and thus the polysoxymetry sensor 108e may detect oxygen saturation of CSF within the spine. In some embodiments, the polysoxymetry sensor 108e may be, or may include, an oximeter, a pulse oximeter, or other suitable components for detecting oxygen saturation of CSF. The polysoxymetry sensor 108e may be configured to detect oxygen saturation of CSF and generate a signal corresponding to the detected oxygen saturation. In some embodiments, the signal generated by the polysoxymetry sensor 108e may be an analog signal, which may be transmitted to the analog-digital converter 112 for conversion to a digital signal. In some embodiments, the signal generated by the polysoxymetry sensor 108e may be a digital signal. The digital signal corresponding to the detected oxygen saturation may be received by the processor(s) 102, which may direct storage of corresponding oxygen saturation data at the data storage 106. In some embodiments, the oxygen saturation data may include numerical data (i.e., numerical values) indicative of the detected oxygen saturation, although other forms of the oxygen saturation data may be used. Detection of oxygen saturation and storage of the oxygen saturation data at the data storage 106 may be carried out as directed by the data logging module 130.

The Raman spectroscopy sensor 108$f$ may be configured to detect a molecular composition of CSF within a region of a patient in which the Raman spectroscopy sensor 108$f$ is positioned. For example, the Raman spectroscopy sensor 108$f$ may be positioned within the cranium of a patient, and thus the Raman spectroscopy sensor 108$f$ may detect a molecular composition of CSF within the cranium. As another example, the Raman spectroscopy sensor 108$f$ may be positioned within the spine of a patient, and thus the Raman spectroscopy sensor 108$f$ may detect a molecular composition of CSF within the spine. In some embodiments, the Raman spectroscopy sensor 108$f$ also may be configured to detect a molecular composition of tissue of the patient when the Raman spectroscopy sensor 108$f$ is positioned within or in contact with the tissue. For example, the Raman spectroscopy sensor 108$f$ may be positioned within parenchymal tissue of the brain of the patient, and thus the Raman spectroscopy sensor 108$f$ may detect a molecular composition of the parenchymal tissue. In some embodiments, the Raman spectroscopy sensor 108$f$ may be, or may include, a spectrometer, a photomultiplier, or other suitable components for detecting a molecular composition of CSF and/or tissue. The Raman spectroscopy sensor 108$f$ may be configured to detect a molecular composition and generate a signal corresponding to the detected molecular composition. In some embodiments, the signal generated by the Raman spectroscopy sensor 108$f$ may be an analog signal, which may be transmitted to the analog-digital converter 112 for conversion to a digital signal. In some embodiments, the signal generated by the Raman spectroscopy sensor 108$f$ may be a digital signal. The digital signal corresponding to the detected molecular composition may be received by the processor(s) 102, which may direct storage of corresponding molecular composition data at the data storage 106. In some embodiments, the molecular composition data may include numerical data (i.e., numerical values) indicative of the detected molecular composition and/or concentration of detected molecules, although other forms of the molecular composition data may be used. Detection of molecular composition and storage of the molecular composition data at the data storage 106 may be carried out as directed by the data logging module 130.

The positional sensor 110 may be configured to detect a positional orientation of a patient. For example, the positional sensor 110 may be configured to detect whether the patient is in a vertical position, a supine position, a prone position, a lateral position, or other position relative to a reference plane. In some embodiments, the positional sensor 110 may include, or may be, a multi-axis positional sensor, such as a three-axis gyroscope, although other suitable types of sensors for detecting a positional orientation of a patient may be used for the positional sensor 110. The positional sensor 110 may be configured to detect a positional orientation of the patient and generate a signal corresponding to the detected positional orientation. In some embodiments, the signal generated by the positional sensor 110 may be an analog signal, which may be transmitted to the analog-digital converter 112 for conversion to a digital signal. In some embodiments, the signal generated by the positional sensor 110 may be a digital signal. The digital signal corresponding to the detected positional orientation may be received by the processor(s) 102, which may direct storage of corresponding positional orientation data at the data storage 106. In some embodiments, the positional orientation data may include numerical data (i.e., numerical values) indicative of the detected positional orientation, although other forms of the positional orientation data may be used. Detection of positional orientation of the patient and storage of the positional orientation data at the data storage 106 may be carried out as directed by the data logging module 130.

The pump(s) 113 may be configured to provide selective micro-metered displacement capabilities activated by the processor 142 to deliver desired amounts of a fluid, such as a therapeutic agent, imaging agent, or CSF, through the catheter(s) 117 either from or to a reservoir(s) 115. The pump 113 may include, without limitation, displacement, reciprocating, peristaltic, diaphragm, capillary or piezoelectric activated components for size minimization. The pump 113 may comprise an actuated microsyringe in communication with the reservoir 115. The pump 113 may be located inside the housing as shown, or outside the housing. The pump 113 may be controlled by the processor in communication with a remote operator (manually or automated) in response to CSF data to deliver a selected amount of therapeutic agent or imaging agent, or to remove a selected amount of CSF, as needed by the patient. The proximal end of the catheter 117 (shown in FIG. 2C) is in fluid communication with the reservoir 115 and pump 113. The distal end of the catheter 117 (not shown) may extend into the anatomical spaces adjacent to any of the sensors 108 for delivery of agents or for the removal of excess CSF.

The antenna(e) 114 may include, without limitation, a cellular antenna for transmitting or receiving signals to/from a cellular network infrastructure, an antenna for transmitting or receiving Wi-Fi signals to/from an access point (AP), a Global Navigation Satellite System (GNSS) antenna for receiving GNSS signals from a GNSS satellite, a Bluetooth antenna for transmitting or receiving Bluetooth signals, a Near Field Communication (NFC) antenna for transmitting or receiving NFC signals, and so forth. The antenna(e) 114 may include any suitable type of antenna depending, for example, on the communications protocols used to transmit or receive signals via the antenna(e) 114. Non-limiting examples of suitable antennae may include directional antennae, non-directional antennae, dipole antennae, folded dipole antennae, patch antennae, multiple-input multiple-output (MIMO) antennae, or the like. The antenna(e) 114 may be communicatively coupled to the one or more transceiver(s) 116 or radio components to which or from which signals may be transmitted or received.

The antenna(e) 114 may include a cellular antenna configured to transmit or receive signals in accordance with established standards and protocols, such as Global System for Mobile Communications (GSM), 3G standards (e.g., Universal Mobile Telecommunications System (UMTS), Wideband Code Division Multiple Access (W-CDMA), CDMA2000, etc.), 4G standards (e.g., Long-Term Evolution (LTE), WiMax, etc.), direct satellite communications, or the like. The antenna(e) 114 may additionally, or alternatively, include a GNSS antenna configured to receive GNSS signals from three or more GNSS satellites carrying time-position information to triangulate a position therefrom. Such a GNSS antenna may be configured to receive GNSS signals from any current or planned GNSS such as, for example, the Global Positioning System (GPS), the GLONASS System, the Compass Navigation System, the Galileo System, or the Indian Regional Navigational System.

The transceiver(s) 116 may include any suitable radio component(s) for—in cooperation with the antenna(e) 114—transmitting or receiving radio frequency (RF) signals in the bandwidth and/or channels corresponding to the communications protocols utilized by the implantable device 100 to communicate with other devices, such as the external device 140 described below. The transceiver(s) 116 may include hardware, software, and/or firmware for modulating, transmitting, or receiving—potentially in cooperation with any of antenna(e) 114—communications signals according to any of the communications protocols discussed above including, but not limited to, one or more Wi-Fi and/or Wi-Fi direct protocols, as standardized by the IEEE 1002.11 standards, one or more non-Wi-Fi protocols, or one or more cellular communications protocols or standards. The transceiver(s) 116 may further include hardware, firmware, or software for receiving GNSS signals. The transceiver(s) 116 may include any known receiver and baseband suitable for communicating via the communications protocols utilized by the implantable device 100. The transceiver(s) 116 may further include a low noise amplifier (LNA), additional signal amplifiers, an analog-to-digital (A/D) converter, one or more buffers, a digital baseband, or the like. Communication between the implantable device 100 and the external device 140 may include transmission of the CSF data (i.e., the pressure data, the flow velocity data, the biochemical data, the oxygen saturation data, the molecular composition data, and/or other data related to CSF) and/or the positional orientation data stored at the data storage 106 from the implantable device 100 to the external device 140. Further, communication between the implantable device 100 and the external device 140 may include transmission of data indicative of sensor detection parameters, data logging parameters, charging parameters, power generation parameters, or other parameters related to operation of the implantable device 100 from the external device 140 to the implantable device 100. Communication between the implantable device 100 and the external device 140 may be carried out as directed by the communication module 132 and/or a corresponding module of the external device 140.

As shown in FIG. 1A, the implantable device 100 may include the one or more power storage device(s) 118 configured to power the processor(s) 102, the memory device(s) 104, the CSF sensor(s) 108, the positional sensor(s) 110, the analog-digital converter(s) 112, antenna(e) 114, the transceiver(s) 116, and/or other components of the device 100. In some embodiments, the one or more power storage device(s) 118 may include one or more batteries, although other suitable types of devices for storing power may be used. In some embodiments, the one or more power storage device(s) 118 may include one or more lithium-ion polymer (Li-Po) batteries. In some embodiments, the one or more power storage device(s) 118 may be rechargeable.

In certain embodiments, the implantable device 100 may include the one or more charging device(s) 120 configured to recharge the one or more power storage device(s) 118. In some embodiments, the one or more charging device(s) 120 may include a wireless electromagnetic induction charger, although other suitable types of devices for recharging the one or more power storage device(s) 118 may be used. In some embodiments, the one or more charging device(s) 120 may cooperate with corresponding components of an external device, such as the external device 140 described below, to facilitate recharging of the one or more power storage device(s) 118. Recharging of the one or more power storage device(s) 118 may be carried out as directed by the power module 134 and/or a corresponding module of the external device.

In certain embodiments, the implantable device 100 may include the one or more power generation device(s) 122 configured to generate power. In some embodiments, the one or more power generation device(s) 122 may generate power for charging the one or more power storage device(s) 118. In some embodiments, the one or more power generation device(s) 122, additionally or alternatively, may generate power for directly powering the processor(s) 102, the memory device(s) 104, the CSF sensor(s) 108, the positional sensor(s) 110, the analog-digital converter(s) 112, antenna(e) 114, the transceiver(s) 116, and/or other components of the device 100. In some embodiments, the one or more power generation device(s) 122 may generate power based at least in part on internal physiological energy present within the patient. For example, the one or more power generation device(s) 122 may generate power based at least in part on cerebrospinal fluid flow within the patient, dural pulsations within the patient, vascular pulsations within the patient, and/or cranial movements of the patient. In some embodiments, the one or more power generation device(s) 122 may be, or may include, a hydraulic power generator disposed within a hollow tube for generating power using CSF flow in a manner similar to a hydroelectric power generator. In some embodiments, the one or more power generation device(s) 122 may be, or may include, a one or more piezoelectric plates for generating power using dural pulsations and/or vascular pulsations. Still other configurations of the one or more power generation device(s) 122 may be used for generating power using internal physiological energy present within the patient. In some embodiments in which the implantable device 100 includes the one or more power generation device(s) 122, the one or more charging device(s) 120 may be omitted. Generation of power by the one or more power generation device(s) 122 may be carried out as directed by the power module 134.

Referring now to illustrative components depicted as being stored in the data storage 106, the O/S 126 may be loaded from the data storage 106 into the memory device 104 and may provide an interface between application software executing on the implantable device 100 and the hardware resources of the implantable device 100. More specifically, the O/S 126 may include a set of computer-executable instructions for managing the hardware resources of the implantable device 100 and for providing common services to application programs (e.g., managing memory allocation among application programs). In certain example embodiments, the O/S 126 may control execution of the other program module(s). The O/S 126 may include any operating system now known or that may be developed in the future.

The DBMS 128 may be loaded into the memory device 104 and may support functionality for accessing, retrieving, storing, and/or manipulating data stored in the memory device 104 and/or data stored in the data storage 106. The DBMS 128 may use any of a variety of database models (e.g., relational model, object model, etc.) and may support any of a variety of query languages. The DBMS 128 may access data represented in one or more data schemas and stored in any suitable data repository including, but not limited to, databases (e.g., relational, object-oriented, etc.), file systems, flat files, distributed datastores in which data is stored on more than one node of a computer network, peer-to-peer network datastores, or the like. The DBMS 128 may be any suitable lightweight DBMS optimized for performance on an implantable device.

Referring now to functionality supported by the various program module(s) depicted in FIG. 1A, the data logging module(s) 130 may include computer-executable instructions, code, or the like that, responsive to execution by the one or more processor(s) 102, may cause the one or more processor(s) 102 to perform functions including, but not limited to, causing the pressure sensor 108a to detect a pressure, causing the flow sensor 108b to detect a flow velocity, causing the viscosity sensor 108c to detect a viscosity, causing the biochemical sensor 108d to detect a biochemical, causing the polsoxymetry sensor 108e to detect an oxygen saturation, causing the Raman spectroscopy sensor 108f to detect a molecular composition, causing the positional sensor 110 to detect a positional orientation, receiving respective signals generated by the pressure sensor 108a, the flow sensor 108b, the viscosity sensor 108c, the biochemical sensor 108d, the polsoxymetry sensor 108e, the Raman spectroscopy sensor 108f, and the positional sensor 110, causing the analog-digital converter 112 to convert respective analog signals into respective digital signals, and storing the CSF data (i.e., the pressure data, the flow velocity data, the biochemical data, the oxygen saturation data, the molecular composition data, and/or other data related to CSF) and the positional orientation data at the data storage 106.

The data logging module 130 may include one or more parameters defining a frequency at which the respective properties are detected by the CSF sensors 108 and the positional sensor 110 and the CSF data and the positional orientation data are stored at the data storage 106. In some embodiments, each of the respective properties may be detected by the CSF sensors 108 and the positional sensor 110 at a frequency of one (1) reading per second, although other frequencies may be used. In this manner, the data stored at the data storage 106 may include CSF data values and positional orientation data values for each one-second interval throughout a monitoring period. In some embodiments, the CSF data values and the positional orientation data values may be stored at the data storage 106 in a table, although other suitable data storage formats may be used. In some embodiments, each entry in the table may include respective CSF data values and a positional orientation data value associated with one another by a common timestamp indicative of the time when the corresponding properties were detected by the CSF sensors 108 and the positional sensor 110.

The communication module(s) 132 may include computer-executable instructions, code, or the like that, responsive to execution by the one or more processor(s) 102, may cause the one or more processor(s) 102 to perform functions including, but not limited to, communicating with one or more external devices, communicating with one or more other implantable devices, such as additional implantable devices 100, transmitting CSF data and positional orientation data to one or more external devices, such as the external device 140, receiving data indicative of sensor detection parameters, data logging parameters, microinjection pumping parameters, charging parameters, power generation parameters, or other parameters related to operation of the implantable device 100 from one or more external devices, such as the external device 140, transmitting or receiving other information or instructions, and the like.

The power module(s) 134 may include computer-executable instructions, code, or the like that, responsive to execution by the one or more processor(s) 102, may cause the one or more processor(s) 102 to perform functions including, but not limited to, determining a charge level of the one or more power storage device(s) 118, causing the one or more charging device(s) 120 to charge the one or more power storage device(s) 118, causing the one or more power generation device(s) 122 to generate power, causing the one or more power generation device(s) 122 to power the processor(s) 102, the memory device(s) 104, the CSF sensor (s) 108, the positional sensor(s) 110, the analog-digital converter(s) 112, pump(s) 113, antenna(e) 114, the transceiver(s) 116, and/or other components of the device 100, causing the one or more power generation device(s) 122 to charge the one or more power storage device(s) 118, and the like.

Figure 1B:
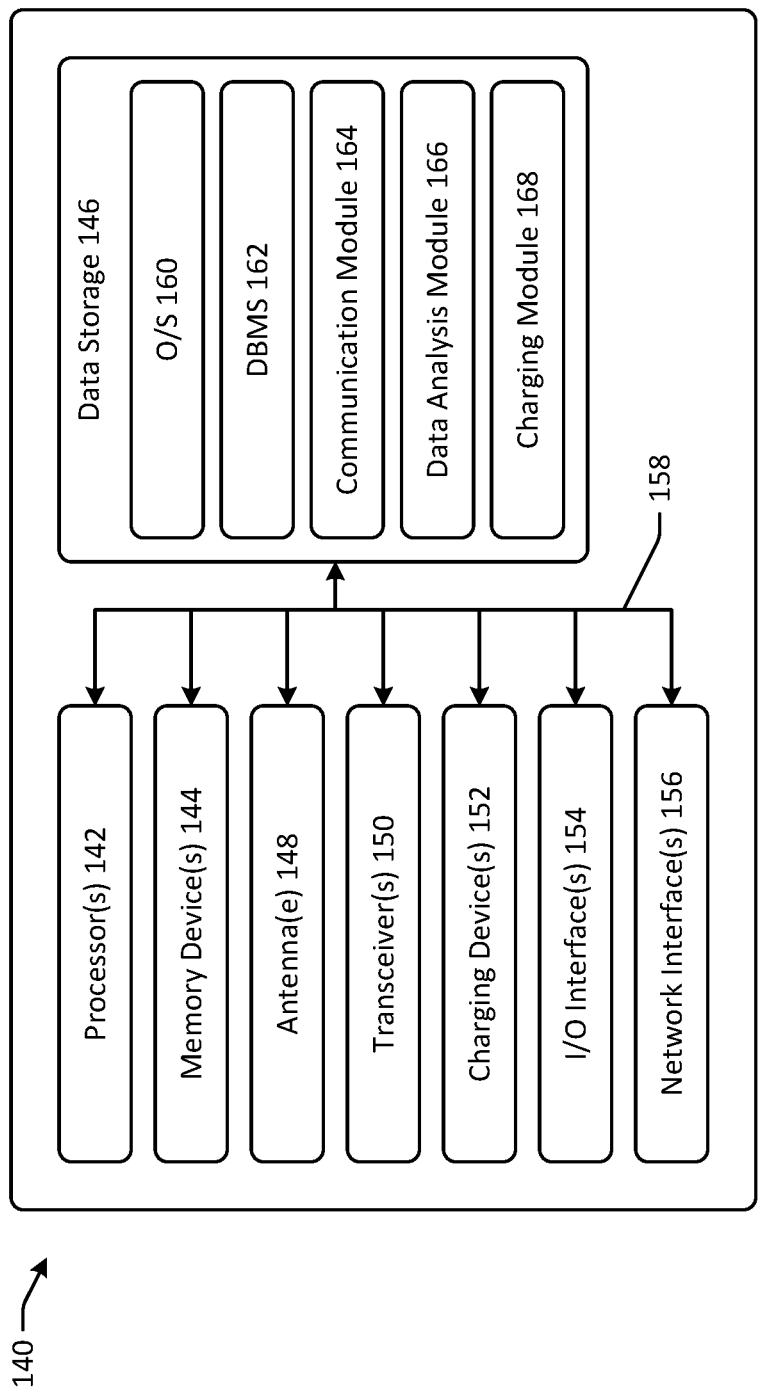
FIG. 1B is a schematic view of an external device for use with the implantable device of FIG. 1A in accordance with one or more embodiments of the disclosure.

FIG. 1B schematically illustrates an example external device 140 (which also may be referred to as a "CSF receiver device," a "receiver device," a "control device," or a "device") configured for use with the implantable device 100 according to one or more embodiments of the disclosure. The external device 140 may be positioned outside of the patient in which the device 100 is implanted and may communicate with the implanted device 100 to carry out various functions described herein. As shown, the external device 140 may include one or more processor(s) 142 (which also may be referred to as a "processing unit"), one or more memory device(s) 144 (which also may be referred to as "memory"), a data storage 146, one or more antenna(e) 148, one or more transceiver(s) 150, one or more charging device(s) 152, one or more input/output interface(s) 154, and one or more network interface(s) 156. The external device 140 also may include one or more bus(es) 158 that functionally couple various components of the external device 140. These components of the external device 140 and their functions are described further below. It will be appreciated that the external device 140 illustrated in FIG. 1B is merely one example of the device 140 described herein, and that various configurations of the device 140 may be used. In some embodiments, certain components illustrated in FIG. 1B may be omitted from the device 140, and, in some embodiments, additional components not illustrated in FIG. 1B may be included in the device 140. The following description may refer to the aforementioned components of the external device 140 in singular form for simplicity, although it will be appreciated that multiple instances of such components may be present in certain embodiments of the device 140.

The processor(s) 142, the memory device(s) 144, the data storage 146, the antenna(e) 148, the transceiver(s) 150, and the bus(es) 158 of the external device 140 generally may be configured in a manner similar to the corresponding components of the implantable device 100 described above.

In certain embodiments, the external device 140 may include the one or more charging device(s) 152 configured to cooperate with the one or more charging device(s) 120 of the implantable device 100 to recharge the one or more power storage device(s) 118. In some embodiments, the one or more charging device(s) 152 may include a wireless electromagnetic induction charger, although other suitable types of devices for recharging the one or more power storage device(s) 118 may be used. For example, the one or more charging device(s) 152 may include a primary induction coil, and the one or more charging device(s) 120 may include a secondary induction coil. During use, the primary induction coil may create an alternating electromagnetic field, and the secondary induction coil may receive energy from the electromagnetic field and convert the energy into electric current for charging the one or more power storage device(s) 118. Recharging of the one or more power storage device(s) 118 may be carried out as directed by the power module 134 of the implantable device 100 and/or a charging module of the external device 140.

The input/output (I/O) interface(s) 154 may facilitate the receipt of input information by the external device 140 from one or more I/O devices as well as the output of information from the external device 140 to the one or more I/O devices. The I/O devices may include any of a variety of components, such as a display or display screen having a touch surface or touchscreen; an audio output device for producing sound, such as a speaker; an audio capture device, such as a microphone; an image and/or video capture device, such as a camera; a haptic unit; and so forth. Any of these components may be integrated into the external device 140 or may be separate. The I/O interface(s) 154 may also include an interface for an external peripheral device connection such as universal serial bus (USB), FireWire, Thunderbolt, Ethernet port or other connection protocol that may connect to one or more networks. The I/O interface(s) 154 may also include a connection to the one or more of antenna(e) 148 to connect to one or more networks via a wireless local area network (WLAN) (such as Wi-Fi) radio, Bluetooth, and/or a wireless network radio, such as a radio capable of communication with a wireless communication network such as a Long Term Evolution (LTE) network, a WiMAX network, a 3G network, etc.

The external device 140 also may include the one or more network interface(s) 156 via which the external device 140 may communicate with any of a variety of other systems, platforms, networks, devices, and so forth. The network interface(s) 156 may enable communication, for example, with one or more wireless routers, one or more host servers, one or more web servers, and the like via one or more networks.

Referring now to functionality supported by the various program module(s) depicted in FIG. 1B, one or more communication module(s) 164 stored at the data storage 146 may include computer-executable instructions, code, or the like that, responsive to execution by the one or more processor(s) 142, may cause the one or more processor(s) 142 to perform functions including, but not limited to, communicating with one or more implantable devices 100, communicating with one or more other external devices, such as additional external devices 140, receiving CSF data and positional orientation data from one or more implantable devices 100, transmitting data indicative of sensor detection parameters, data logging parameters, charging parameters, power generation parameters, or other parameters related to operation of the implantable device 100 to one or more implantable devices 100, transmitting or receiving other information or instructions, and the like.

One or more data analysis module(s) 166 stored at the data storage 146 may include computer-executable instructions, code, or the like that, responsive to execution by the one or more processor(s) 142, may cause the one or more processor(s) 142 to perform functions including, but not limited to, processing CSF data and positional orientation data received from one or more implantable devices 100, identifying changes in respective CSF data values and/or positional orientation values received from a particular implantable device 100 during a monitoring period, comparing respective CSF data values received from a particular implantable device 100 to predetermined CSF data value ranges, identifying respective CSF data values that are greater than or less than the corresponding predetermined CSF data value ranges, comparing respective CSF data values received from a first implantable device 100 implanted in a patient and respective CSF data values received from a second implantable device 100 implanted in the patient, identifying one or more differences between the respective CSF data values received from the first implantable device 100 and the respective CSF data values received from the second implantable device 100, and the like.

One or more charging module(s) 168 stored at the data storage 146 may include computer-executable instructions, code, or the like that, responsive to execution by the one or more processor(s) 142, may cause the one or more processor(s) 142 to perform functions including, but not limited to, causing the one or more charging device(s) 150 to cooperate with the one or more charging device(s) 120 to charge the one or more power storage device(s) 118, and the like.

It should be appreciated that the program module(s), applications, computer-executable instructions, code, or the like depicted in FIGS. 1A and 1B as being stored in the data storage 106 of the implantable device 100 and the data storage 146 of the external device 140 are merely illustrative and not exhaustive, and that the processing described as being supported by any particular module may alternatively be distributed across multiple module(s) or performed by a different module. In addition, various program module(s), script(s), plug-in(s), Application Programming Interface(s) (API(s)), or any other suitable computer-executable code hosted locally on the implantable device 100 or the external device 140, and/or hosted on other computing device(s) accessible via one or more networks, may be provided to support the functionality provided by the program module (s), applications, or computer-executable code depicted in FIGS. 1A and 1B and/or additional or alternate functionality. Further, functionality may be modularized differently such that processing described as being supported collectively by the collection of program module(s) depicted in FIGS. 1A and 1B may be performed by a fewer or greater number of module(s), or functionality described as being supported by any particular module may be supported, at least in part, by another module. In addition, program module(s) that support the functionality described herein may form part of one or more applications executable across any number of systems or devices in accordance with any suitable computing model. In addition, any of the functionality described as being supported by any of the program module(s) depicted in FIGS. 1A and 1B may be implemented, at least partially, in hardware and/or firmware.

FIGS. 2A-2C illustrate an example implantable device 100 and components thereof according to one or more embodiments of the disclosure. As shown, the implantable device 100 may include the one or more processor(s) 102, the one or more memory device(s) 104, the data storage 106, the one or more CSF sensor(s) 108, the one or more positional sensor(s) 110, the one or more analog-digital converter(s) 112, the one or more pump(s) 113, the one or more antenna(e) 114, the one or more reservoir(s) 115, the one or more transceiver(s) 116, the one or more catheter(s) 117, the one or more power storage device(s) 118, the one or more charging device(s) 120, and the one or more power generation device(s) 122 described above. The implantable device 100 also may include the one or more bus(es) 124 described above, which are not shown in FIGS. 2A-2C for purposes of illustration.

As shown in FIGS. 2A-2C, the implantable device 100 also may include a housing 170 (which also may be referred to as a "case") and a support member 172 (which also may be referred to as a "sensor support member" or a "sensor support"). The housing 170 may extend along a central axis $A_C$ of the implantable device 100, as shown. The housing 170 may include a base 174 and a cover 176 attached to one another. In some embodiments, the base 174 and the cover 176 may be fixedly attached to one another, for example, by welding or other means of permanent attachment. In other embodiments, the base 174 and the cover 176 may be removably attached to one another, for example, by mating threads, fasteners, or other means of removable attachment. In some embodiments, as shown, the base 174 may be formed as a cup-shaped member, and the cover 176 may be formed as a disc-shaped member that is positioned over the open end of the base 174. In this manner, the base 174 and the cover 176 may define an interior space of the housing 170 for containing other components of the implantable device 100 therein. In some embodiments, an interface between the base 174 and the cover 176 may be sealed, for example, by one or more elastomeric seals, to inhibit bodily fluids from entering the interior space of the housing 170. Additional seals also may be used for sealing interfaces between the housing 170 and one or more components extending through apertures defined in the housing 170 (i.e., components extending through the housing 170 from the interior space to outside of the housing 170). In some embodiments, the housing 170 may have a cylindrical shape, as shown, although other suitable shapes of the housing 170 may be used. The housing 170 may be formed of various biocompatible materials, including one or more biocompatible metals, polymers, or ceramics. As shown, the implantable device 100 also may include one or more fasteners 178 for attaching the housing 170, and thus the overall device 100, to a patient. In some embodiments, the fasteners 178 may be screws, such as bone screws, although other suitable types of mechanical fasteners may be used. In some embodiments, as shown, the housing 170 may include mating apertures defined therein, such as through the cover 176, for receiving the fasteners 178 to facilitate attachment of the housing 170 to the patient.

As shown, the processor 102, the memory device 104, the data storage 106, the analog-digital converter 112, the pump 113, the antenna 114, the transceiver 116, the reservoir 117, the power storage device 118, and the charging device 120 may be disposed within the housing 170. In other words, these components may be positioned within the interior space of the housing 170. It will be appreciated that the illustrated arrangement of the processor 102, the memory device 104, the data storage 106, the analog-digital converter 112, the pump 113, the antenna 114, the reservoir 115, the transceiver 116, the power storage device 118, and the charging device 120 is merely one example, and that other arrangements of these components may be used. In some embodiments, the positional sensor 110 also may be disposed within the housing 170. In other embodiments, the positional sensor 110 may be disposed outside of, or at least partially outside of, the housing 170 and attached thereto. As explained above, in certain embodiments, the positional sensor 110 may be a gyroscope. In some embodiments, the power generation device 122 may be disposed within the housing 170. In other embodiments, the power generation device 122 may be positioned outside of the housing 170 and attached thereto. In still other embodiments, the power generation device 122 may be disposed partially within and partially outside of the housing 170. For example, a portion of the power generation device 122 may extend through a mating aperture defined in the distal end of the base 174. In this manner, the power generation device 122 may contact bodily fluids and/or anatomical features of the patient to facilitate generation of power, as described above. In such embodiments, the interface between the power generation device 122 and the housing 170 may include one or more seals to inhibit bodily fluids from entering the interior space of the housing 170.

The support member 172 may extend from the housing 170, as shown. In some embodiments, the support member 172 may extend along the central axis $A_C$ of the implantable device 100, although other positions of the support member 172 may be used. In some embodiments, as shown, the support member 172 may be flexible, such that at least a portion of the support member 172 is configured to move relative to the housing 170, such as by pending the portion of the support member 172. For example, a proximal portion of the support member 172 may be fixedly attached to the housing 170, such as the base 174 thereof, and a distal portion of the support member 172 may be configured to bend relative to the housing 170. As described further below, the movement of the support member 172 relative to the housing 170 may allow the sensors 108 or catheters 117 to be placed in various regions of the patient. In some embodiments, the support member 172 may be formed of an elastomeric material, a flexible metal, or a flexible polymer. The support member 172 may have a natural or original state but may be moved relative to the housing 170 from the natural state to a second state, as shown via dashed lines in FIG. 1A, by applying a force to the support member 172. In some embodiments, the support member 172 may be deflected or elastically deformed from the natural state to the second state when a force is applied, but the support member 172 may return to the natural state upon removal of the force. In other embodiments, the support member 172 may be moved or deformed from the natural state to the second state when a force is applied, and the support member 172 may maintain the second state absent additional forces or energy being applied thereto. For example, the support member 172 may be formed of a shape-memory alloy or a shape-memory polymer. As shown, the support member 172 may be formed as an elongated member having a cylindrical shape, although other shapes and configurations of the support member 172 may be used. In some embodiments, as shown, the support member 172 may be formed as a tube. In other embodiments, the support member 172 may be formed as a wire. In some embodiments, the support member 172 may be disposed partially within the housing 170 and partially outside of the housing 170. For example, the support member 172 may extend through a mating aperture defined in the distal end of the base 174. In such embodiments, the interface between the support member 172 and the housing 170 may include one or more seals to inhibit bodily fluids from entering the interior space of the housing 170.

As shown in FIGS. 2A-2C, the sensors 108 or catheters 117 may be disposed outside of the housing 170 and attached to the support member 172. The sensors 108 may include one or more, or all, of the pressure sensor 108a, the flow sensor 108b, the viscosity sensor 108c, the biochemical sensor 108d, the polsoxymetry sensor 108e, and the Raman spectroscopy sensor 108f described above, in any combination. Although the illustrated embodiment shows three of the sensors 108, any number of the sensors 108 may be used. In some embodiments, as shown, the sensors 108 or catheters 117 may be spaced apart from the housing 170, in particular the distal end of the base 174. In some embodiments, the sensors 108 or catheters 117 may be positioned at or near the distal end of the support member 172. In some embodiments, the sensors 108 or catheters 117 may be spaced apart from the distal end of the support member 172. In some embodiments, the sensors 108 or catheters 117 may be positioned closer to the distal end of the support member 172 than the proximal end of the support member 172. Various positions of the sensors 108 or catheters 117 along the support member 172 may be used. In some embodiments, one or more of the sensors 108 or catheters 117 may be positioned at or near the distal end of the support member 172, one or more of the sensors 108 or catheters 117 may be positioned at or near the proximal end of the support member 172, and/or one or more of the sensors 108 or catheters 117 may be positioned between the distal end and the proximal end of the support member 172, along an intermediate portion thereof. In some embodiments, as shown, the sensors 108 or catheters 117 may be fixedly attached to the support member 172, such as by an adhesive, bonding, or mechanical means of attachment. In other embodiments, the sensors 108 or catheters 117 may be removably attached to the support member 172. As explained above, the support member 172 may be configured to move relative to the housing 170. Accordingly, the sensors 108 or catheters 117 also may be configured to move relative to the housing 170 along with the support member 172. In some embodiments, the implantable device 100 may include a plurality of the support members 172 each extending from the housing 170 and attached thereto. In such embodiments, the respective support members 172 each may have one or more of the sensors 108 or catheters 117 attached thereto, and the support members 172 may be configured to move relative to one another. In this manner, the sensors 108 may be placed at different target locations within a patient. For example, one of the sensors 108 or catheters 117 attached to one of the support members 172 may be placed within a first target location of a patient, and another one of the sensors 108 or catheters 117 attached to another one of the support members 172 may be placed within a second target location of the patient.

Figure 3A:
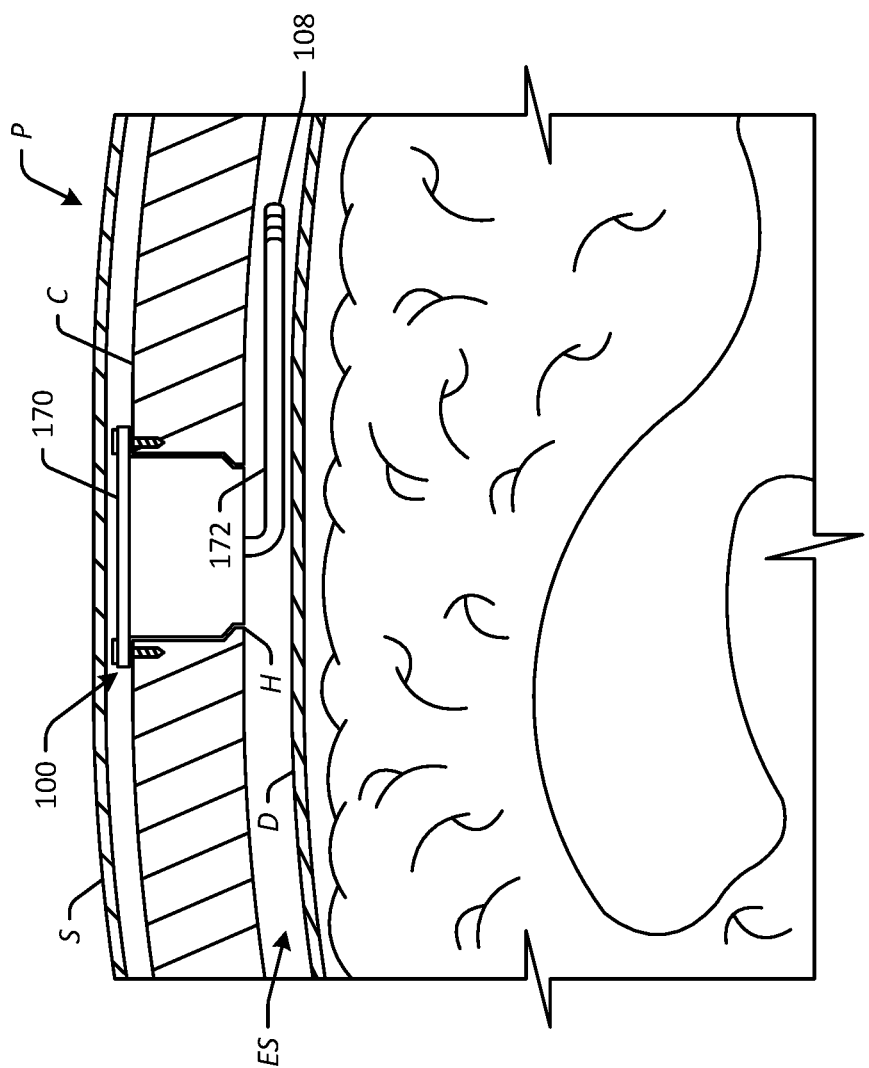
FIG. 3A is a partial cross-sectional side view of the implantable device of FIG. 2A implanted within a patient, illustrating an epidural placement of one or more of the sensors of the implantable device.

FIGS. 3A-3D illustrate implantation of the implantable device 100 within a patient P according to embodiments of the disclosure. As explained above, the support member 172 may be configured to move relative to the housing 170, and thus the support member 172 may assume a number of different orientations relative to the housing 170. In this manner, the support member 172 may be moved in order to position the sensors 108 of the device 100 within one or more target locations of the patient P. The catheters 117 can be disposed in configurations as described herein for the sensors 108. In some embodiments, the sensors 108 may be formed of radiopaque materials or may include markers formed of radiopaque materials. In this manner, positions of the sensors 108 may be visualized by a clinician during implantation of the device 100. FIG. 3A illustrates an example cranial implantation of the device 100 and epidural placement of the sensors 108. As shown, the device 100 may be positioned beneath the skin S of the patient P, and the housing 170 may be attached to the cranium C of the patient P via the fasteners 178. In some embodiments, as shown, a hole H may be formed through the cranium C, for example, using a burr or other surgical tool. The housing 170 may be positioned at least partially within the hole H. For example, the base 174 may be positioned at least partially within the hole H, while the cover 176 is positioned outside of the hole H against the outer surface of the cranium C. In some embodiments, as shown, the distal end of the housing 170 may be flush or substantially flush with the inner surface of the cranium C. In other embodiments, the distal end of the housing 170 may be positioned within the hole H or may extend beyond the inner surface of the cranium C. As shown in FIG. 3A, the support member 172 may be moved from the natural position to a second position in which a majority of the support member 172 extends transverse to the central axis $A_C$ of the device 100. In some embodiments, a guide tool may be used to move the support member 172 relative to the housing 170, such that the support member 172 assumes the illustrated configuration. As shown, the sensors 108 may be positioned within an epidural space ES of the patient P, between the cranium C and the dura mater D. As shown, the sensors 108 may be laterally spaced apart from the hole H. In this manner, scar tissue, which generally may form around the hole H, may be less likely to deform, damage, or otherwise interfere with operation of the sensors 108. Upon implantation, the device 100 may monitor various properties of CSF, as described above, within the epidural space ES.

Figure 3B:
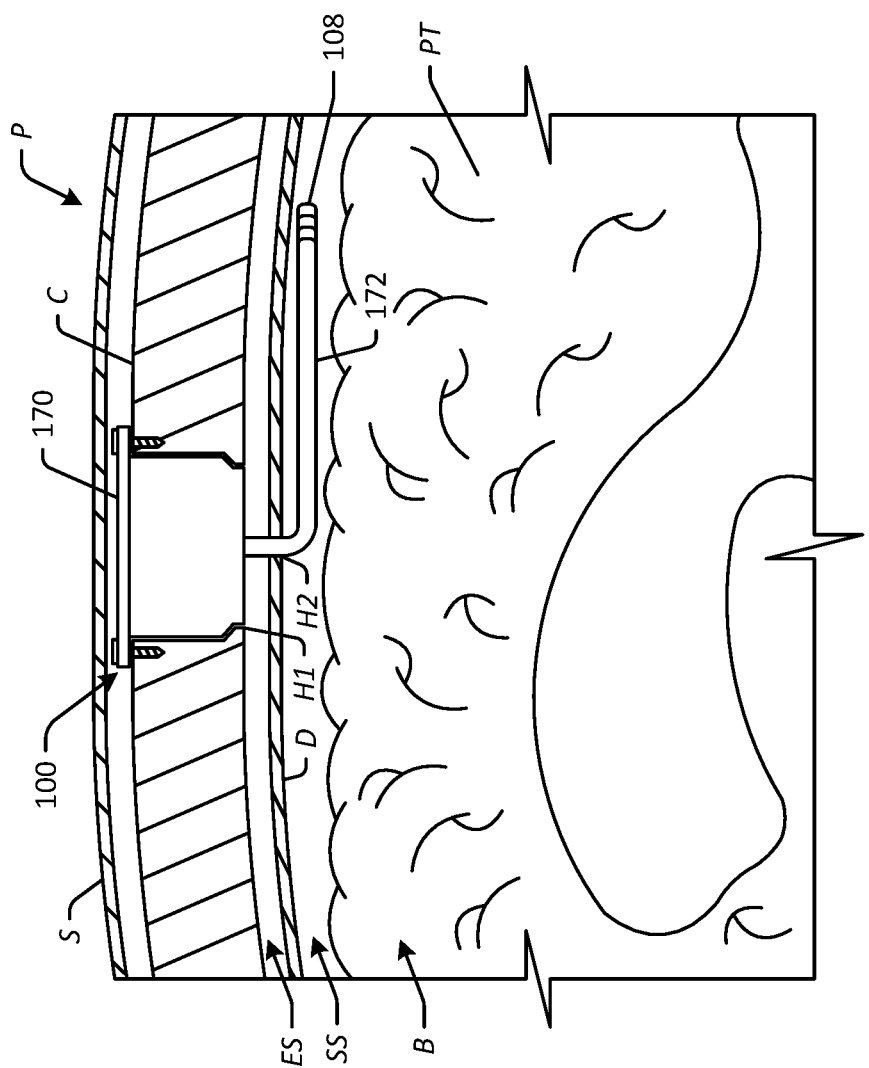
FIG. 3B is a partial cross-sectional side view of the implantable device of FIG. 2A implanted within a patient, illustrating a subdural placement of one or more of the sensors of the implantable device.

FIG. 3B illustrates an example cranial implantation of the device 100 and subdural placement of the sensors 108. The device 100 generally may be positioned in a manner similar to that described above with respect to FIG. 3A, with the housing 170 attached to the cranium C of the patient P via the fasteners 178 and positioned at least partially within a first hole H1 formed through the cranium C. As shown in FIG. 3B, the support member 172 may extend through a second hole H2 formed through the dura mater D and into a subdural space SS of the patient P. The support member 172 may be moved from the natural position to a second position in which a majority of the support member 172 extends transverse to the central axis $A_C$ of the device 100. In some embodiments, a guide tool may be used to guide the support member 172 through the second hole H2 and to move the support member 172 relative to the housing 170, such that the support member 172 assumes the illustrated configuration. As shown, the sensors 108 may be positioned within the subdural space SS of the patient P, between the dura mater D and the parenchymal tissue PT of the brain B. As shown, the sensors 108 may be laterally spaced apart from the second hole H2. In this manner, scar tissue, which generally may form around the second hole H2, may be unlikely to deform, damage, or otherwise interfere with operation of the sensors 108. Upon implantation, the device 100 may monitor various properties of CSF, as described above, within the subdural space SS.

Figure 3C:
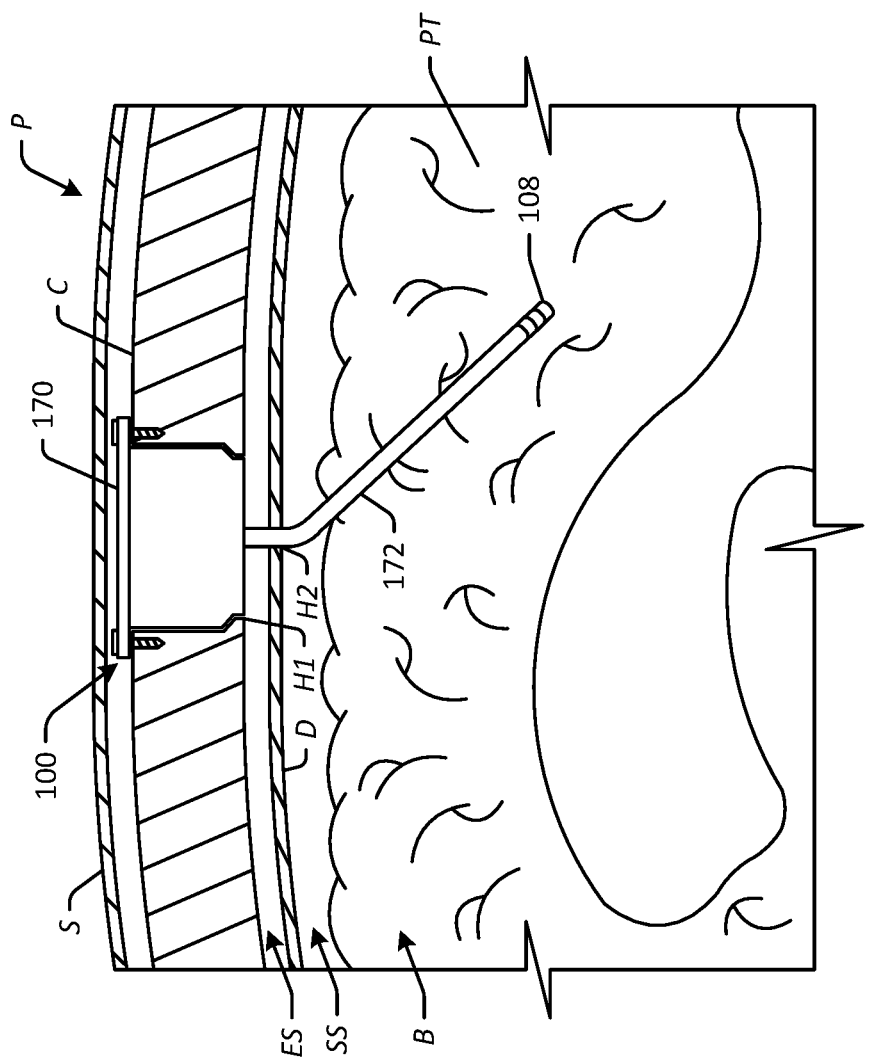
FIG. 3C is a partial cross-sectional side view of the implantable device of FIG. 2A implanted within a patient, illustrating an intraparenchymal placement of one or more of the sensors of the implantable device.

FIG. 3C illustrates an example cranial implantation of the device 100 and intraparenchymal placement of the sensors 108. The device 100 generally may be positioned in a manner similar to that described above with respect to FIG. 3B, with the housing 170 attached to the cranium C of the patient P via the fasteners 178 and positioned at least partially within a first hole H1 formed through the cranium C. As shown in FIG. 3C, the support member 172 may extend through a second hole H2 formed through the dura mater D and into the parenchymal tissue PT of the brain B. The support member 172 may be moved from the natural position to a second position in which a majority of the support member 172 extends transverse to the central axis $A_C$ of the device 100. In some embodiments, a guide tool may be used to guide the support member 172 through the second hole H2 and into the parenchymal tissue PT and to move the support member 172 relative to the housing 170, such that the support member 172 assumes the illustrated configuration. As shown, the sensors 108 may be positioned within the parenchymal tissue PT of the patient P. Upon implantation, the device 100 may monitor various properties of CSF, as described above, within the parenchymal tissue PT and/or properties of the parenchymal tissue PT.

Figure 3D:
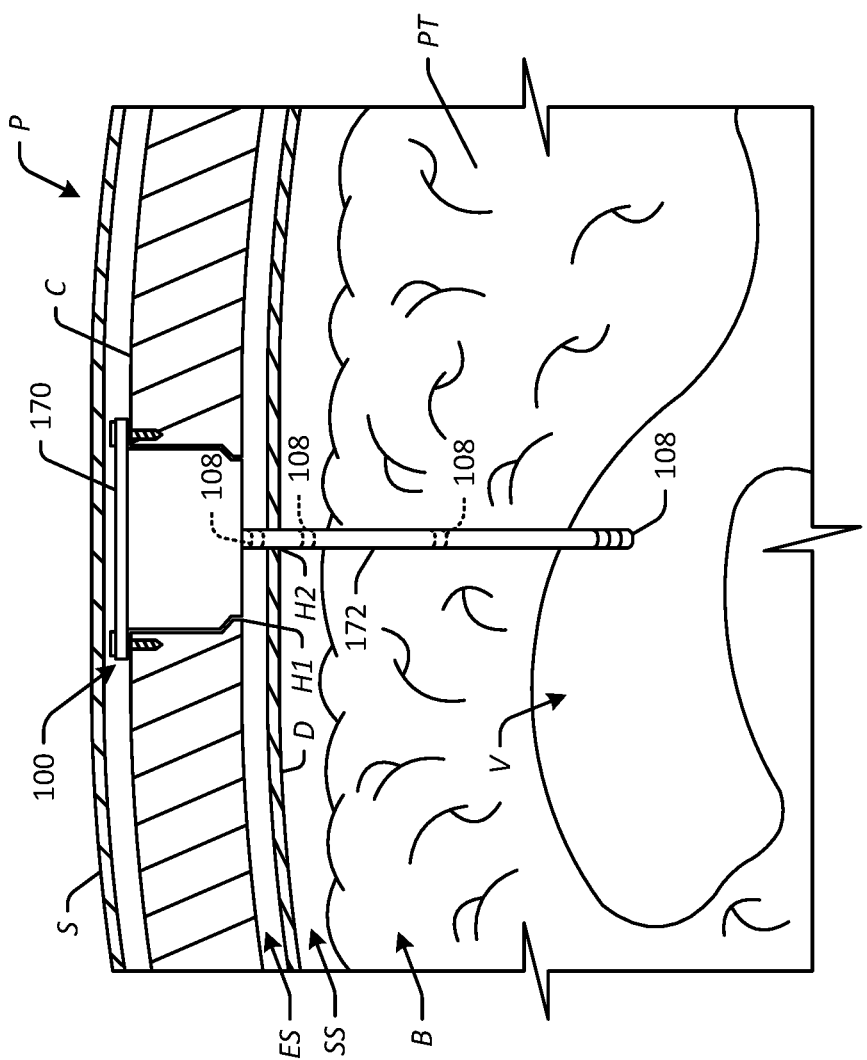
FIG. 3D is a partial cross-sectional side view of the implantable device of FIG. 2A implanted within a patient, illustrating an intraventricular placement of one or more of the sensors of the implantable device.

FIG. 3D illustrates an example cranial implantation of the device 100 and intraventricular placement of the sensors 108. The device 100 generally may be positioned in a manner similar to that described above with respect to FIG. 3C, with the housing 170 attached to the cranium C of the patient P via the fasteners 178 and positioned at least partially within a first hole H1 formed through the cranium C. As shown in FIG. 3D, the support member 172 may extend through a second hole H2 formed through the dura mater D, through the parenchymal tissue PT, and into a ventricle V of the brain B. According to various embodiments, the ventricle V may be the left lateral ventricle, the right lateral ventricle, the third ventricle, or the fourth ventricle of the brain B. In some embodiments, the support member 172 may be maintained in the natural position, with the support member 172 extending coaxially with the central axis $A_C$ of the device 100. In other embodiments, the support member 172 may be moved from the natural position to a second position in which a majority of the support member 172 extends transverse to the central axis $A_C$ of the device 100. In some embodiments, a guide tool may be used to guide the support member 172 through the second hole H2, through the parenchymal tissue PT, and into the ventricle V, and/or to move the support member 172 relative to the housing 170, such that the support member 172 assumes the illustrated configuration. As shown, the sensors 108 may be positioned within the ventricle V of the patient P. Upon implantation, the device 100 may monitor various properties of CSF, as described above, within the ventricle V.

In certain embodiments, the implantable device 100 may include a plurality of the sensors 108 positioned at different locations along the support member 172, which may allow different sensors 108 to be placed within different target locations of the patient P. For example, FIG. 3D illustrates additional sensors 108 via dashed lines, with the sensors 108 being spaced apart from one another at different locations along the support member 172. In this manner, one or more of the sensors 108 may be placed within the epidural space ES of the patient P, one or more of the sensors 108 may be placed within the subdural space SS of the patient P, one or more of the sensors 108 may be placed within the parenchymal tissue PT of the patient P, and one or more of the sensors 108 may be placed within the ventricle V of the patient P. Various combinations of positioning of the sensors 108 along the support member 172 and placement of the sensors 108 within different target locations of the patient P may be used in different embodiments. In this manner, the implantable device 100 may be used to monitor various properties of CSF simultaneously within different regions of the patient P.

It will be appreciated that placement of the sensors 108 within the different regions of the patient P described above may have certain advantages and disadvantages as compared to one another. For example, epidural placement of the sensors 108 may be the least invasive placement, may be relatively easy to achieve, and may present a relatively low risk of meningitis and bleeding. However, epidural placement of the sensors 108 may be the least accurate placement for detecting CSF pressure, may allow a degree of scar tissue formation around the sensors 108, may not allow for detecting certain CSF properties described above, and may not be suitable for long-term use. Subdural placement of the sensors 108 may be minimally invasive and relatively easy to achieve, may allow for detecting flow velocity of CSF, may present a relatively low risk of bleeding, and may be suitable for long-term use. However, subdural placement of the sensors 108 may be less accurate than intraparenchymal and intraventricular placement for detecting CSF pressure, and may allow a degree of scar tissue formation around the sensors 108. Intraparenchymal placement of the sensors 108 may be more accurate than epidural and subdural placement for detecting CSF pressure, and may allow for detection of biochemistry and pulse oximetry of the parenchymal tissue. However, intraparenchymal placement of the sensors 108 may be more invasive than epidural and subdural placement, may present a moderate risk of bleeding, may allow a degree of scar tissue formation around the sensors 108, and may not allow for detecting certain CSF properties described above, such as CSF flow velocity. Intraventricular placement of the sensors 108 may be the most accurate for detecting CSF pressure, and may present no risk of scar tissue formation around the sensors 108. However, intraventricular placement of the sensors 108 may be the most invasive placement, and may present a moderate risk of bleeding. In view of these considerations, clinicians and/or researchers may select a particular placement of the sensors 108 for a given patient. Additionally, in certain instances, the implantable device 100 may include multiple sensors 108 spaced apart from one another for placement within different regions of the patient, thereby obtaining different types of CSF data from respective regions of the patient, as described above.

It will be appreciated that the implantations of the device 100 illustrated in FIGS. 3A-3D are merely examples, and that various other implantations of the device 100 may be used, either in the cranium or other regions of a patient. For example, in some embodiments, the device 100 may be implanted in the spine of a patient. In such embodiments, the housing 170 may be attached to the spine, such as one or more vertebrae thereof, and the sensors 108 may be positioned within the central canal or the subarachnoid space of the spine. In some instances, multiple devices 100 may be implanted in a single patient. For example, multiple devices 100 may be implanted in different regions of the cranium to monitor CSF properties of the respective regions and allow for comparison of the CSF data for the respective regions of the cranium. In another example, one or more devices 100 may be implanted in the cranium, and one or more devices may be implanted in the spine of a patient to monitor CSF properties of the respective regions and allow for comparison of the CSF data for the cranium and the spine.

In embodiments, the invention provides devices and methods for treating one or more pathologies by administering to the patient an effective amount of a therapeutic agent from a reservoir disposed within the housing in operable communication with a pump controlled by the processor to selectively dispense the therapeutic agent therefrom into a catheter extending outside of the housing into the cerebrospinal fluid. In embodiments, the invention provides devices and methods for treating one or more pathologies by withdrawing from the patient an effective amount of cerebrospinal fluid to a reservoir disposed within the housing in operable communication with a pump controlled by the processor to selectively withdraw the cerebrospinal fluid within a catheter attached thereto and extending outside of the housing into the cerebrospinal fluid. Various other uses and implantation methods of the implantable device 100 may be contemplated in view of the foregoing description and the accompanying drawings.

Although specific embodiments of the disclosure have been described, one of ordinary skill in the art will recognize that numerous other modifications and alternative embodiments are within the scope of the disclosure. For example, any of the functionality and/or processing capabilities described with respect to a particular device or component may be performed by any other device or component. Further, while various illustrative implementations and architectures have been described in accordance with embodiments of the disclosure, one of ordinary skill in the art will appreciate that numerous other modifications to the illustrative implementations and architectures described herein are also within the scope of this disclosure.

Program module(s), applications, or the like disclosed herein may include one or more software components including, for example, software objects, methods, data structures, or the like. Each such software component may include computer-executable instructions that, responsive to execution, cause at least a portion of the functionality described herein (e.g., one or more operations of the illustrative methods described herein) to be performed.

A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution. Other examples of programming languages include, but are not limited to, a macro language, a shell or command language, a job control language, a script language, a database query or search language, or a report writing language. In one or more example embodiments, a software component comprising instructions in one of the foregoing examples of programming languages may be executed directly by an operating system or other software component without having to be first transformed into another form.

A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution). Software components may invoke or be invoked by other software components through any of a wide variety of mechanisms. Invoked or invoking software components may comprise other custom-developed application software, operating system functionality (e.g., device drivers, data storage (e.g., file management) routines, other common routines and services, etc.), or third-party software components (e.g., middleware, encryption, or other security software, database management software, file transfer or other network communication software, mathematical or statistical software, image processing software, and format translation software). Software components associated with a particular solution or system may reside and be executed on a single platform or may be distributed across multiple platforms. The multiple platforms may be associated with more than one hardware vendor, underlying chip technology, or operating system. Furthermore, software components associated with a particular solution or system may be initially written in one or more programming languages, but may invoke software components written in another programming language.

Computer-executable program instructions may be loaded onto a special-purpose computer or other particular machine, a processor, or other programmable data processing apparatus to produce a particular machine, such that execution of the instructions on the computer, processor, or other programmable data processing apparatus causes one or more functions or operations specified in the flow diagrams to be performed. These computer program instructions may also be stored in a computer-readable storage medium (CRSM) that upon execution may direct a computer or other programmable data processing apparatus to function in a particular manner, such that the instructions stored in the computer-readable storage medium produce an article of manufacture including instruction means that implement one or more functions or operations specified in the flow diagrams. The computer program instructions may also be loaded onto a computer or other programmable data processing apparatus to cause a series of operational elements or steps to be performed on the computer or other programmable apparatus to produce a computer-implemented process.

Additional types of CRSM that may be present in any of the devices described herein may include, but are not limited to, programmable random access memory (PRAM), SRAM, DRAM, RAM, ROM, electrically erasable programmable read-only memory (EEPROM), flash memory or other memory technology, compact disc read-only memory (CD-ROM), digital versatile disc (DVD) or other optical storage, magnetic cassettes, magnetic tape, magnetic disk storage or other magnetic storage devices, or any other medium which can be used to store the information and which can be accessed. Combinations of any of the above are also included within the scope of CRSM. Alternatively, computer-readable communication media (CRCM) may include computer-readable instructions, program module(s), or other data transmitted within a data signal, such as a carrier wave, or other transmission. However, as used herein, CRSM does not include CRCM.

Although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment. The term "based at least in part on" and "based on" are synonymous terms that may be used interchangeably herein.

That which is claimed is:

1. An implantable device for monitoring properties of cerebrospinal fluid of a patient, the implantable device comprising:
   a housing configured for attaching to the patient;
   a processor disposed within the housing;
   a support member extending from the housing, at least a portion of the support member being configured to move relative to the housing;
   one or more sensors disposed outside of the housing and attached to the support member, the one or more sensors in operable communication with the processor and configured to detect one or more properties of cerebrospinal fluid, wherein the one or more sensors comprise a pulse oximetry sensor configured to detect oxygen saturation or a Raman spectroscopy sensor configured to detect a molecular composition of cerebrospinal fluid; and a data storage disposed within the housing, the data storage in operable communication with the processor and configured to store cerebrospinal fluid data corresponding to the one or more properties.

2. The implantable device of claim 1, wherein the support member comprises a flexible tube configured to bend relative to the housing.

3. The implantable device of claim 1, wherein the support member comprises a flexible wire configured to bend relative to the housing.

4. The implantable device of claim 1, wherein the support member comprises a proximal portion and a distal portion, wherein the proximal portion is fixedly attached to the housing, and wherein the distal portion is configured to move relative to the housing.

5. The implantable device of claim 1, wherein the one or more sensors comprise a pressure sensor configured to detect a pressure of cerebrospinal fluid.

6. The implantable device of claim 5, wherein the pressure sensor comprises a fiber-optic sensor.

7. The implantable device of claim 1, wherein the one or more sensors comprise a flow sensor configured to detect a flow velocity of cerebrospinal fluid.

8. The implantable device of claim 7, wherein the flow sensor comprises a linear tube, a discoid member, or a thermometer.

9. The implantable device of claim 1, wherein the one or more sensors comprise a viscosity sensor configured to detect a viscosity of cerebrospinal fluid.

10. The implantable device of claim 9, wherein the viscosity sensor comprises a tube.

11. The implantable device of claim 1, wherein the one or more sensors comprise a biochemical sensor configured to detect one or more biomarkers of chronic neurological diseases.

12. The implantable device of claim 11, wherein the biochemical sensor is configured to detect beta-amyloid, tau protein, alpha-synuclein, lactic acid, glucose, electrolytes, enzymes, neurotransmitters, bacterial or viral DNA or RNA.

13. The implantable device of claim 1, wherein the one or more sensors comprise the pulse oximetry sensor configured to detect oxygen saturation.

14. The implantable device of claim 1, wherein the one or more sensors comprise the Raman spectroscopy sensor configured to detect a molecular composition of cerebrospinal fluid.

15. The implantable device of claim 1, further comprising a positional sensor in operable communication with the processor and configured to detect a positional orientation of the patient, wherein the data storage is further configured to store positional data in association with the cerebrospinal fluid data.

16. The implantable device of claim 15, wherein the positional sensor comprises a gyroscope disposed within the housing.

17. An implantable device for monitoring properties of cerebrospinal fluid of a patient, the implantable device comprising:
    a housing configured for attaching to the patient;
    a processor disposed within the housing;
    a support member extending from the housing, at least a portion of the support member being configured to move relative to the housing;
    one or more sensors disposed outside of the housing and attached to the support member, the one or more sensors in operable communication with the processor and configured to detect one or more properties of cerebrospinal fluid; and
a data storage disposed within the housing, the data storage in operable communication with the processor and configured to store cerebrospinal fluid data corresponding to the one or more properties further comprising a reservoir disposed within the housing and configured for containing a therapeutic agent or imaging agent in operable communication with a pump and the processor to selectively dispense the therapeutic agent or the imaging agent therefrom into a catheter extending into the cerebrospinal fluid.

18. The implantable device of claim 1, further comprising a transceiver in operable communication with the processor and the data storage, wherein the transceiver is configured to transmit the cerebrospinal fluid data to an external device positioned outside of the patient.

19. The implantable device of claim 1, further comprising:
    a power storage device disposed within the housing and configured to power the processor and the one or more sensors; and
    a power generation device in operable communication with the power storage device and configured to generate power for at least one of: (i) charging the power storage device; and (ii) powering the processor and the one or more sensors.

20. The implantable device of claim 1, wherein the power generation device is configured to generate power based at least in part on at least one of: (i) cerebrospinal fluid flow within the patient; (ii) dural pulsations within the patient; (iii) vascular pulsations within the patient; and (iv) cranial movements of the patient.

21. An implantable device for monitoring properties of cerebrospinal fluid of a patient, the implantable device comprising:
    a housing configured for attaching to the patient;
    a processor disposed within the housing;
    a plurality of sensors disposed outside of the housing and configured to move relative to the housing, the plurality of sensors in operable communication with the processor and configured to detect one or more properties of cerebrospinal fluid;
    a data storage disposed within the housing, the data storage in operable communication with the processor and configured to store cerebrospinal fluid data corresponding to the one or more properties; and
    a reservoir disposed within the housing and configured for containing a therapeutic agent or imaging agent in operable communication with a pump and the processor to selectively dispense the therapeutic agent or the imaging agent therefrom into a catheter extending outside of the housing into the cerebrospinal fluid.

22. The implantable device of claim 21, wherein the plurality of sensors further comprises at least one of: (i) a pressure sensor configured to detect a pressure of cerebrospinal fluid ii) a flow sensor configured to detect a flow velocity of cerebrospinal fluid; (iii) a viscosity sensor configured to detect a viscosity of cerebrospinal fluid; (iv) a biochemical sensor configured to detect one or more biomarkers of chronic neurological diseases; (v) a pulse oximetry sensor configured to detect oxygen saturation; and (vi)

a Raman spectroscopy sensor configured to detect a molecular composition of cerebrospinal fluid.

23. The implantable device of claim 22, wherein the plurality of sensors further comprises:
   a flow sensor configured to detect a flow velocity of cerebrospinal fluid;
   a viscosity sensor configured to detect a viscosity of cerebrospinal fluid;
   a biochemical sensor configured to detect one or more biomarkers of chronic neurological diseases;
   a pulse oximetry sensor configured to detect oxygen saturation; and
   a Raman spectroscopy sensor configured to detect a molecular composition of cerebrospinal fluid.

24. The implantable device of claim 21, further comprising a positional sensor fixed relative to the housing, wherein the positional sensor is in operable communication with the processor and configured to detect a positional orientation of the patient, and wherein the data storage is further configured to store positional data in association with the cerebrospinal fluid data.

25. An implantable device for monitoring properties of cerebrospinal fluid of a patient, the implantable device comprising:
   a housing configured for attaching to the patient;
   a processor disposed within the housing;
   one or more sensors disposed outside of the housing, the one or more sensors in operable communication with the processor and configured to detect one or more properties of cerebrospinal fluid;
   a data storage disposed within the housing, the data storage in operable communication with the processor and configured to store cerebrospinal fluid data corresponding to the one or more properties; and
   a power generation device attached to the housing, the power generation device configured to generate power for powering the processor and the one or more sensors, and wherein the power generation device is configured to generate power based at least in part on at least one of: (i) cerebrospinal fluid flow within the patient; (ii) dural pulsations within the patient; (iii) vascular pulsations within the patient; and (iv) cranial movements of the patient.

26. The implantable device of claim 25, further comprising a power storage device in operable communication with the processor, the one or more sensors, and the power generation device, wherein the power generation device is further configured to generate power for charging the power storage device.

* * * * *